(12) United States Patent
Nelson

(10) Patent No.: US 9,173,609 B2
(45) Date of Patent: Nov. 3, 2015

(54) BRAIN CONDITION MONITORING BASED ON CO-ACTIVATION OF NEURAL NETWORKS

(75) Inventor: Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 218 days.

(21) Appl. No.: 13/446,598

(22) Filed: Apr. 13, 2012

(65) Prior Publication Data

US 2012/0271148 A1    Oct. 25, 2012

Related U.S. Application Data

(60) Provisional application No. 61/477,363, filed on Apr. 20, 2011.

(51) Int. Cl.
| | |
|---|---|
| *A61B 5/00* | (2006.01) |
| *A61N 1/36* | (2006.01) |
| *A61B 5/04* | (2006.01) |
| *A61B 5/0476* | (2006.01) |
| *A61B 5/055* | (2006.01) |

(52) U.S. Cl.
CPC ............ *A61B 5/4064* (2013.01); *A61N 1/3606* (2013.01); *A61N 1/36139* (2013.01); *A61B 5/04008* (2013.01); *A61B 5/0476* (2013.01); *A61B 5/055* (2013.01); *A61B 5/4088* (2013.01); *A61N 1/36064* (2013.01); *A61N 1/36067* (2013.01); *A61N 1/36082* (2013.01); *A61N 1/36171* (2013.01)

(58) Field of Classification Search
CPC .. A61B 5/04008; A61B 5/0476; A61B 5/055; A61B 5/4064; A61B 5/4088; A61N 1/3606; A61N 1/36064; A61N 1/36067; A61N 1/36082; A61N 1/36139; A61N 1/3671

USPC ............ 600/544, 545, 411, 410, 407; 607/45, 607/59
See application file for complete search history.

(56) References Cited

U.S. PATENT DOCUMENTS

| | | | |
|---|---|---|---|
| 4,227,516 A | 10/1980 | Meland et al. | |
| 4,753,246 A | 6/1988 | Freeman | |
| 4,776,345 A | 10/1988 | Cohen et al. | |
| 5,299,569 A | 4/1994 | Wernicke et al. | |
| 6,157,857 A | 12/2000 | Dimpfel | |

(Continued)

OTHER PUBLICATIONS

Zhou et al., "Divergent network connectivity changes in behavioural variant frontotemporal dementia and Alzheimer's disease", Brain, vol. 133, 2010, pp. 1352-1367.*

(Continued)

*Primary Examiner* — Katherine Fernandez
(74) *Attorney, Agent, or Firm* — Shumaker & Sieffert, P.A.

(57) ABSTRACT

A brain condition can be tracked based on identification of co-activation of two antagonistic networks of a patient's brain. Various embodiments concerns methods and devices for sensing one or more signals indicative of brain activity, detecting one or more episodes of default mode network activation based on the one or more signals, detecting one or more episodes of salience network activation based on the one or more signals, and identifying one or more episodes of temporal co-activation of the default mode network and the salience network based on the detected one or more episodes of default mode network activation and the one or more episodes of salience network activation. The brain condition can be tracked and treated based on the identification of the one or more episodes of co-activation.

29 Claims, 5 Drawing Sheets

(56) References Cited

U.S. PATENT DOCUMENTS

| | | | |
|---|---|---|---|
| 6,167,298 | A | 12/2000 | Levin |
| 6,200,273 | B1 | 3/2001 | Sininger |
| 6,227,203 | B1 | 5/2001 | Rise et al. |
| 6,402,520 | B1 | 6/2002 | Freer |
| 6,453,193 | B1 | 9/2002 | Heyrend et al. |
| 6,615,076 | B2 | 9/2003 | Mitra |
| 6,920,351 | B2 | 7/2005 | Mitra |
| 7,006,872 | B2 | 2/2006 | Gielen et al. |
| 7,089,059 | B1 | 8/2006 | Pless |
| 7,120,486 | B2 | 10/2006 | Leuthardt |
| 7,171,339 | B2 | 1/2007 | Repucci |
| 7,257,439 | B2 | 8/2007 | Llinas |
| 7,280,867 | B2 | 10/2007 | Osorio et al. |
| 7,341,562 | B2 | 3/2008 | Pless |
| 7,392,079 | B2 | 6/2008 | Donoghue |
| 7,409,321 | B2 | 8/2008 | Repucci |
| 7,532,935 | B2 | 5/2009 | Maschino et al. |
| 7,577,472 | B2 | 8/2009 | Li et al. |
| 7,626,015 | B2 | 12/2009 | Feinstein |
| 7,668,591 | B2 | 2/2010 | Lee et al. |
| 7,734,340 | B2 | 6/2010 | DeRidder |
| 7,747,318 | B2 | 6/2010 | John |
| 7,801,601 | B2 | 9/2010 | Maschino et al. |
| 7,818,065 | B2 | 10/2010 | Llinas |
| 7,819,812 | B2 | 10/2010 | John |
| 7,892,182 | B2 | 2/2011 | Pless |
| 7,894,890 | B2 | 2/2011 | Sun et al. |
| 7,894,903 | B2 | 2/2011 | John |
| 7,937,138 | B2 | 5/2011 | Liley |
| 8,017,764 | B2 | 9/2011 | Feinstein |
| 8,073,534 | B2 | 12/2011 | Low |
| 8,078,281 | B2 | 12/2011 | Priori |
| 8,090,674 | B2 | 1/2012 | Ginosar |
| 8,140,152 | B2 | 3/2012 | John |
| 8,364,272 | B2 * | 1/2013 | Goetz .............................. 607/45 |
| 2001/0003145 | A1 | 6/2001 | Mori et al. |
| 2004/0073129 | A1 | 4/2004 | Caldwell et al. |
| 2004/0073273 | A1 | 4/2004 | Gluckman et al. |
| 2005/0033154 | A1 | 2/2005 | deCharms |
| 2005/0154424 | A1 | 7/2005 | Tass |
| 2005/0197560 | A1 | 9/2005 | Rao et al. |
| 2005/0209512 | A1 | 9/2005 | Heruth et al. |
| 2005/0215884 | A1 | 9/2005 | Greicius et al. |
| 2005/0283053 | A1 | 12/2005 | deCharms |
| 2006/0155348 | A1 | 7/2006 | deCharms |
| 2006/0173259 | A1 | 8/2006 | Flaherty |
| 2006/0212090 | A1 | 9/2006 | Lozano et al. |
| 2007/0067003 | A1 | 3/2007 | Sanchez |
| 2007/0123758 | A1 | 5/2007 | Miesel et al. |
| 2007/0142874 | A1 | 6/2007 | John |
| 2007/0191704 | A1 | 8/2007 | deCharms |
| 2007/0225674 | A1 | 9/2007 | Molnar et al. |
| 2007/0244407 | A1 | 10/2007 | Osorio |
| 2008/0001600 | A1 | 1/2008 | deCharms |
| 2008/0015459 | A1 | 1/2008 | Llinas |
| 2008/0045775 | A1 | 2/2008 | Lozano |
| 2008/0071150 | A1 | 3/2008 | Miesel et al. |
| 2008/0077039 | A1 | 3/2008 | Donnett |
| 2008/0243022 | A1 | 10/2008 | Donnett |
| 2008/0269631 | A1 | 10/2008 | Denison et al. |
| 2009/0082691 | A1 | 3/2009 | Denison et al. |
| 2009/0099623 | A1 | 4/2009 | Bentwich |
| 2009/0105521 | A1 | 4/2009 | Bentwich |
| 2009/0124919 | A1 | 5/2009 | Ginosar et al. |
| 2009/0163982 | A1 | 6/2009 | deCharms |
| 2009/0177144 | A1 | 7/2009 | Masmanidis et al. |
| 2009/0179642 | A1 | 7/2009 | decharms |
| 2009/0192556 | A1 | 7/2009 | Wu et al. |
| 2009/0196471 | A1 | 8/2009 | Goetz |
| 2009/0220425 | A1 | 9/2009 | Moxon |
| 2009/0318794 | A1 | 12/2009 | deCharms |
| 2009/0318826 | A1 | 12/2009 | Green et al. |
| 2010/0069739 | A1 | 3/2010 | deCharms |
| 2010/0100153 | A1 | 4/2010 | Carlson |
| 2010/0114237 | A1 | 5/2010 | Giftakis et al. |
| 2010/0121213 | A1 | 5/2010 | Giftakis et al. |
| 2010/0121214 | A1 | 5/2010 | Giftakis et al. |
| 2010/0121215 | A1 | 5/2010 | Giftakis |
| 2010/0135553 | A1 | 6/2010 | Joglekar |
| 2010/0137937 | A1 | 6/2010 | John et al. |
| 2010/0185220 | A1 * | 7/2010 | Naghavi et al. ................ 606/158 |
| 2010/0241020 | A1 | 9/2010 | Zaidel et al. |
| 2010/0262205 | A1 | 10/2010 | DeRidder |
| 2010/0280334 | A1 | 11/2010 | Carlson et al. |
| 2010/0280335 | A1 | 11/2010 | Carlson et al. |
| 2010/0280336 | A1 | 11/2010 | Giftakis et al. |
| 2010/0280403 | A1 | 11/2010 | Erdogmus |
| 2010/0286748 | A1 | 11/2010 | Midani |
| 2011/0105584 | A1 | 5/2011 | Feinstein et al. |
| 2011/0130797 | A1 | 6/2011 | Talathi et al. |
| 2011/0137371 | A1 | 6/2011 | Giftakis et al. |
| 2011/0144716 | A1 | 6/2011 | Bikson et al. |
| 2011/0184489 | A1 | 7/2011 | Nicolelis et al. |
| 2011/0196446 | A1 | 8/2011 | Wu et al. |
| 2011/0218454 | A1 | 9/2011 | Low |
| 2011/0257715 | A1 | 10/2011 | Jarosh et al. |
| 2012/0083700 | A1 * | 4/2012 | Osorio .......................... 600/483 |

OTHER PUBLICATIONS

Serge et al., "Altered Resting State Networks in Mild Cognitive Impairment and Mild Alzheimer's Disease: An fMRI Study", Human Brain Mapping, vol. 26, 2005, pp. 231-239.*

Mulert et al., "Integration of fMRI and simultaneous EEG: towards a comprehensive understanding of localization and time-course of brain activity in target detection", NeuroImage, vol. 22, 2004, pp. 83-94.*

Sridharan et al., "A critical role for the right fronto-insular cortex in switching between central-executive and default-mode networks", Proceedings of the National Academy of Sciences of the United States of America, vol. 105, No. 34, pp. 12569-12574.*

Loddenkkemper, et al., "Circadian Patterns of Pediatric Seizures," Neurology 76, Jan. 11, 2011: 145-153.

Eusebio, et al., "Resonance in Subthalamo-Cortical Circuits in Parkinson's Disease", Brain 2009, pp. 1-12.

Garrett et al., The Importance of Being Variable, The Journal of Neuroscience, Mar. 23, 2011, 31(12): 4496-4503.

Keimel et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease," Neuromol Med (2010) 12:27-43.

Van Veen, et al., "Localization of Brain Electrical Activity via Linearly Constrained Minimum Variance Spatial Filtering" IEEE Transactions on Biomedical Engineering, vol. 44, No. 9, Sep. 1997.

Westlye, et al., "Increased Hippocampal Default Mode Synchronization During Rest in Middle-Aged and Elderly APOE ε4 Carriers: Relationships with Memory Performance," The Journal of Neuroscience, May 25, 2011, 31(21): 7775-7783.

* cited by examiner

300

400

BRAIN CONDITION MONITORING BASED ON CO-ACTIVATION OF NEURAL NETWORKS

PRIORITY

This application claims the benefit of U.S. Provisional Application No. 61/477,363, entitled "BRAIN CONDITION MONITORING BASED ON CO-ACTIVATION OF NEURAL NETWORKS" and filed on Apr. 20, 2011, the entire contents of which are incorporated herein by reference.

TECHNICAL FIELD

The disclosure relates to medical systems, and, more particularly, medical systems that monitor brain activation of a patient.

BACKGROUND

Implantable medical devices, such as electrical stimulation devices, may be used in different therapeutic applications, such as for deep brain stimulation (DBS), spinal cord stimulation (SCS), pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain, tremor, Alzheimer's disease, Parkinson's disease, other types of movement disorders, seizure disorders (e.g., epilepsy), urinary or fecal incontinence, sexual dysfunction, obesity, mood disorders, gastroparesis, or diabetes. In some therapy systems, an implantable electrical stimulator delivers electrical therapy to a target tissue site within a patient with the aid of one or more electrodes, which may be deployed by medical leads.

SUMMARY

In general, the disclosure relates to methods, systems, and devices for monitoring activation of a patient's brain, and more specifically, tracking episodes of co-activation of the brain's default mode network and salience network. This can be used to monitor various diseases, such as Alzheimer's disease, and in some cases direct a course of therapy.

Various embodiments concern a method for tracking a condition of a patient's brain, comprising: monitoring one or more first areas of the patient's brain, each of the one or more first areas associated with providing default mode network function for the patient's brain; identifying one or more episodes of default mode network activation of the one or more first areas, the identified one or more episodes of default mode network activation associated with default mode network function; monitoring one or more second areas of the patient's brain, each of the one or more second areas associated with providing salience network function for the patient's brain, wherein the one or more first areas of the patient's brain are different from the one or more second areas of the patient's brain; identifying one or more episodes of salience network activation of the one or more second areas, the identified one or more episodes of salience network activation associated with salience network function; identifying a plurality of episodes of temporal co-activation of the first and second brain areas based on the identification of the one or more episodes of default mode network activation and the identification of the one or more episodes of salience network activation; and tracking a condition of the patient's brain based on the plurality of episodes of temporal co-activation, wherein identifying the plurality of episodes of co-activation and tracking the condition are each performed at least in part by medical device control circuitry. In some of the method embodiments, each of the one or more episodes of default mode network activation is identified based on a first signal crossing a first threshold indicative of default mode network activation; and each of the one or more episodes of salience network activation is identified based on a second signal crossing a second threshold indicative of salience network activation, wherein in some cases the first threshold is dynamically changed based on the second signal and the second threshold is dynamically changed based on the first signal.

In some of the method embodiments, monitoring the one or more first areas of the patient's brain and monitoring the one or more second areas of the patient's brain comprises sensing one or more bioelectrical brain signals or imaging the patient's brain with one or more of fMRI, MEG, and PET. In some of the method embodiments, each of the episodes of temporal co-activation of the first and second brain areas is identified based on temporal co-activation occurring for at least a predetermined period of time. In some of the method embodiments, tracking the condition of the patient's brain based on the plurality of episodes of temporal co-activation comprises identifying the presence of a disease, and in some cases tracking the condition comprises measuring progression of a disease state based on one or both of frequency and duration of the plurality of episodes of temporal co-activation. In some cases, the condition comprises Alzheimer's disease.

Some of the method embodiments include administering a therapy based on the tracking of the condition of the patient's brain, and some cases include titrating a therapy that treats the condition based on whether the tracking of the condition of the patient's brain indicates a worsening or easing of the condition.

Various embodiments concern a system comprising: one or more sensors configured to receive one or more signals indicative of brain activity; and control circuitry comprising a processor and memory, the memory having program instructions executable by the processor stored therein, the control circuitry configured to detect one or more episodes of default mode network activation based on the one or more signals, detect one or more episodes of salience network activation based on the one or more signals, and identify one or more episodes of temporal co-activation of the default mode network and the salience network based on the detected one or more episodes of default mode network activation and the detected one or more episodes of salience network activation. In various system embodiments, the control circuitry is configured to control a therapy based on the identification of the one or more episodes of temporal co-activation of the default mode network and the salience network.

In some of the embodiments, the control circuitry is configured to: track a brain condition based on the identification of the one or more episodes of temporal co-activation of the default mode network and the salience network; and indicate a worsening of the brain condition based on an increase in one or both of frequency and duration of the one or more episodes of temporal co-activation. In some embodiments, the control circuitry is configured to: detect each of the one or more episodes of default mode network activation based on a first parameter of the one or more of signals crossing a first threshold indicative of default mode network activation; and detect each of the one or more episodes of salience network activation based on a second parameter of the one or more of signals crossing a second threshold indicative of salience network activation. In some cases, the one or more signals comprise bioelectrical brain signals. In some of the method embodiments, the one or more sensors are part of a brain imaging system; the control circuitry detects the one or more episodes of default mode network activation based on activation of one or more brain areas associated with default mode network function; and the control circuitry detects the one or more episodes of salience network activation based on activation of one or more brain areas associated with salience network function. In some of the embodiments, the control circuitry is configured to identify each of the one or more episodes of temporal co-activation based on temporal co-activation of the default mode network and the salience network that persists for at least a predetermined period of time.

Various embodiments concern a system, comprising: means for sensing one or more signals indicative of brain activity; means for detecting one or more episodes of default mode network activation based on the one or more signals; means for detecting one or more episodes of salience network activation based on the one or more signals; and means for identifying one or more episodes of temporal co-activation of the default mode network and the salience network based on the detected one or more episodes of default mode network activation and the one or more episodes of salience network activation. Some of the embodiments include means for controlling a therapy based on the identification of the one or more episodes of temporal co-activation of the default mode network and the salience network. Some of the embodiments include means for tracking a brain condition based on the identification of the one or more episodes of temporal co-activation of the default mode network and the salience network, wherein a worsening brain condition is indicated based on an increase in one or both of frequency and duration of the one or more episodes of temporal co-activation.

Various embodiments concern a physically embodied computer-readable medium comprising instructions executable by a processor to cause a medical device to: monitor activation of a default mode network of a brain; monitor activation of a salience network of the brain; identify one or more episodes of temporal co-activation of the default mode network and the salience network; and track a brain condition based on identification of the one or more episodes of co-activation of the default mode network and the salience network.

The details of one or more examples are set forth in the accompanying drawings and the description below. Other features, objects, and advantages will be apparent from the description and drawings, and from the claims.

DETAILED DESCRIPTION

Figure 1:
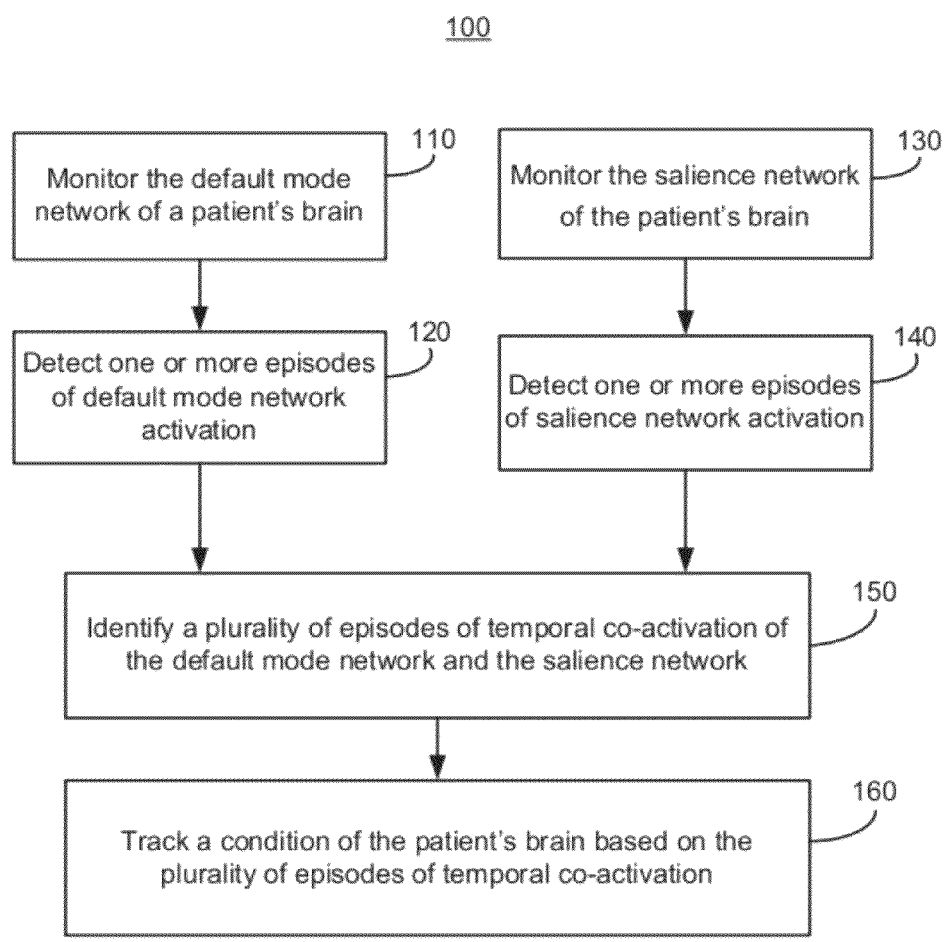
FIG. 1 is a flow diagram demonstrating various aspects of tracking a condition of a patient's brain based on network co-activation.

The methods, systems, and devices described herein provide for tracking and/or treating a brain condition by monitoring co-activation of different networks of the brain.

Alzheimer's disease is a type of dementia marked by worsening memory and cognitive impairment. Alzheimer's disease may manifest in short term memory impairment, inattentiveness, apathy, and mild cognitive and motor difficulties in early stages. Midterm stages of Alzheimer's disease can include impairment of speech and complex motor skills, delusion, long term memory loss, and moderate cognitive impairment. Advanced stages can include the total loss of language, discernable cognition, and the ability to care for oneself for even the most simple of matters. The complications of Alzheimer's disease are often contributing factors in death. There is no consensus on the cause of Alzheimer's disease and there is no recognized cure.

While each patient's Alzheimer's disease onset and progression of symptoms are different, the above symptoms, as well as other symptoms, can be used to track progression of the disease. Tracking the progression of Alzheimer's disease through observation, both by the patient and other people (e.g., family and/or health professionals) of these impairment-type symptoms can be difficult and inconsistent. Such tracking is subjective, hard to quantify, and in some cases is dependent on the self-reflection and self-reporting abilities of the patient. Tracking the progression of Alzheimer's disease through such observation can further be complicated by patients who have frequent and inexplicable fluctuations between "good days" of relatively less impairment and "bad days" of relatively greater impairment. Moreover, to the extent that such observation of symptoms of Alzheimer's disease only tracks an outward manifestation of Alzheimer's disease, then such techniques often miss pre- and early Alzheimer's disease phases.

The present disclosure provides, among other things, an objective measure of Alzheimer's disease and other brain conditions. Various embodiments of the present disclosure concern tracking a condition of a patient's brain by monitoring both a default mode network function and a salience network function of the patient's brain. The condition is tracked by identifying episodes of co-activation of the patient's default mode network and salience network. Quantitative measures of co-activation can be calculated based on frequency, length, and total time per day of co-activation, among others. Generally, more frequent and longer episodes of co-activation are indicative of a worsening brain condition, such as Alzheimer's disease, while less frequent and shorter episodes of co-activation are indicative of an improving or relatively better brain condition. The efficacy of one or more therapies treating the underlying brain condition, or treating the symptoms, can be evaluated using various embodiments of the present disclosure. Moreover, various therapies can be titrated or otherwise controlled based on the tracking of a brain condition in accordance with the present disclosure.

The brain is comprised of various networks interconnected by neurons. Some of these networks may activate or deactivate to carry out a function and/or induce a particular state of mind. The neurons of the networks may depolarize ("fire") in coordination (e.g., at a specific oscillatory frequency) and generate bioelectrical activity. One network may interact with other brain networks in coordination or antagonism to support proper brain function. Two of these networks are the default mode network and the salience network.

The default mode network, as referred to herein, refers to a neural network that provides an offline processing mode during resting behavioral states and is reciprocal in function to the active processes of the salience network. The function of the default mode network allows the brain to stay on-line without other parts of the brain, such as those associated with cognition, being active. In healthy individuals, activation of the default mode network is normally reduced during cognitively intense activity, such as memory encoding, but the default mode network is more active during states where cognition and memory functions are not actively engaged. The default mode network may be thought of as an idling process, whereby in a healthy brain the nuclei/locations/clusters of the default mode network are active while the cognitive areas of the brain are relatively inactive. The default mode network may be particularly active when a person is conscious but is not currently entertaining a conscious thought or prevailing perception. A person who has mindlessly stared at a wall or lost his or her train of thought for a period of time may have activation of his or her default mode network during these episodes.

The default mode network function of a person's brain can be provided by one area, or more likely multiple areas, of the person's brain. The areas of a person's brain that provide the default mode network function can be distributed in numerous ways, and likely in different ways for different people. As such, the default mode network, at least at the present understanding, does not have a certain anatomical location within the greater brain structure across all individuals. However, it is believed that the areas of the brain that provide default mode network functionality are generally located in the medial and lateral parietal regions extending into posterior cingulate and retrosplenial cortices, and midline and lateral frontal brain regions, and are unlikely to be located in the cortical area.

The salience network, as referred to herein, refers to a brain network that provides conscious and mainline functions of the brain. The function of the salience network allows the brain to actively analyze input (e.g., consciously appreciate what a person is seeing) and contemplate, among other active processes. As such, actively listening to a person talk, reading, recalling a certain memory, deliberating, watching an event unfold, and talking are examples of functions that are actively supported by the salience network. Deactivation of the default mode network, in coordination with hippocampal or similar cognitive activation, may be required for focused attention and successful encoding of memories. The anatomical areas of the salience network are distributed in various areas of the brain and differ from person to person. However, it is thought that areas of the brain that actively support the salience network are generally located in the cortical areas and more specifically in the motor cortex. The hippocampus, as previously mentioned, is a sensing target for monitoring the salience network.

The default mode network and salience network can operate, in a healthy individual, in a push-pull relationship. Being that the two networks have reciprocal functions it is thought that both networks should not be activated at the same time. For example, during certain times one network may be activated while the other is operating minimally or not at all, and at certain other times the other of the two networks is activated while the other network operates minimally or not at all. One or both of these networks may play an active role in suppressing the other network to carry out the push-pull relationship. For example, the default mode network may shut down or suppress other areas of the brain, such as the salience network, when appropriate to allow the brain to idle.

The activations of the default mode network and salience networks may be inversely related, such that one ramps down while the other ramps up or are otherwise activated at different times. A well functioning relationship between the default mode network and the salience network in support of proper brain function may vary from person to person. However, it is believed that activation of both networks at the same time is not supportive of proper brain function and is indicative of a problematic brain condition.

It is noted that a portion of brain tissue may be associated with several brain functions. For example, a specific portion of a person's brain may support sleep functions as well as salience network functions. Likewise, portions of the brain that actively support default mode network function may also actively support other brain functions. However, it is believed that the areas of a person's brain associated with salience network function do not generally overlap with those areas associated with default mode network function. As such, because of the antagonistic relationship of the default mode network and salience network, and their role in supporting cognition, temporal co-activation of these networks can indicate improper brain function. Furthermore, more frequent and/or longer periods of co-activation can indicate a worsening brain condition. Co-activation can be identified using various techniques. FIGS. 1-4 illustrate flow charts demonstrating several embodiments for identifying and addressing co-activation, among other things.

FIG. 1 illustrates a flow chart of a method 100 for detecting network co-activation and tracking a brain condition. The method 100 includes monitoring 110 the default mode network of a patient's brain. In parallel to default mode network monitoring 110 is monitoring 130 the salience network of the patient's brain. Such monitoring (110 and 130) can be implemented using the various techniques described herein. Based on the default mode network monitoring 110, one or more episodes of default mode network activation can be detected 120. Likewise, the salience network monitoring 130 can be used to detect 140 one or more episodes of salience network activation.

Based on the detected 120 episodes of default mode network activation and the detected 140 episodes of salience network activation, a plurality of episodes of temporal co-activation of the default mode and salience networks can be identified 150. Such co-activation can be identified 150 by recognizing that both networks were active at the same time. For example, monitoring (110 and 130) and detecting (120 and 140) can be performed in real-time such that the concurrent activation of both the default mode network and the salience network can be identified 150. In some embodiments, however, default mode network and salience network activation detection (120 and 140) can be performed at a later time. The monitored (110 and 130) episode data and/or default mode network and salience network activation detection (120 and 140) information can be time stamped to allow for later temporal comparison of default mode network and salience network activation episodes to identify 150 the co-activation between the episodes.

Various criteria are contemplated for tracking 160 a brain condition. For example, co-activation episodes can be tracked 160 based on a time parameter (e.g., minutes per day of co-activation), rate parameter (e.g., episodes of co-activation per hour or day), or time of day of co-activation (at night or during the day), among other options. Tracking 160 can include determining when the amount of co-activation becomes inappropriate co-activation, understanding that minor occasional co-activation may occur in a healthy individual. As such, a first criterion could be used to identify an episode of co-activation (e.g., amplitude threshold of a bioelectrical brain signal or a power threshold relating to the frequency of oscillation of the bioelectrical brain signal) and another could be used to declare inappropriate co-activation (e.g., co-activation lasting longer than 1 minute or totaling more than 2 hours in a day).

In some embodiments, only 1 episode of co-activation will be identified 150 and used to characterize a brain condition, such as an especially prolonged episode, an episode showing multiple different indicators of co-activation, and/or a parameter of co-activation showing an especially high indication of co-activation. However, it is believed that a plurality of episodes of co-activation will be especially useful in tracking 160 the brain condition. Tracking 160 may include, among other things, trending the frequency, length, and/or intensity of the plurality of episodes of co-activation to characterize the brain condition. More frequent, longer, and more intense (e.g., a parameter of co-activation showing an especially high indication of co-activation) episodes of co-activation may be associated with a worsening brain condition. Tracking 160 may include providing an output to a printer or display indicating the co-activation episodes and/or indicating that a brain condition has been assessed to be improving or worsening.

Tracking 160 may also include making and outputting a brain condition diagnosis, such as Alzheimer's disease, based on the co-activation. For example, if greater frequency, length, and/or intensity of the plurality of episodes of co-activation correlate to worsening memory and/or cognitive abilities, then a diagnosis may be made. In particular, a diagnosis may be made that the brain condition is of the type characterized by increased co-activation of different brain networks. As such, tracking 160 may include differentiating disease pathologies. For example, there are many types of dementia, and the techniques disclosed herein may be used to determine which of various types is underlying a brain condition for a particular patient (e.g., by determining whether or not the brain condition is associated with inappropriate co-activation), which may drive treatment decisions for the patient. The techniques of the present disclosure may determine that a level of co-activation for a patient correlate to worsening memory and/or cognitive abilities of the patient, including that co-activation may underlie the disease for that patient. In some embodiments, based on the condition tracking 160, an indication that a particular treatment to control co-activation episodes may be beneficial may be made by a clinician or automatically by control circuitry of a medical device.

Figure 2:
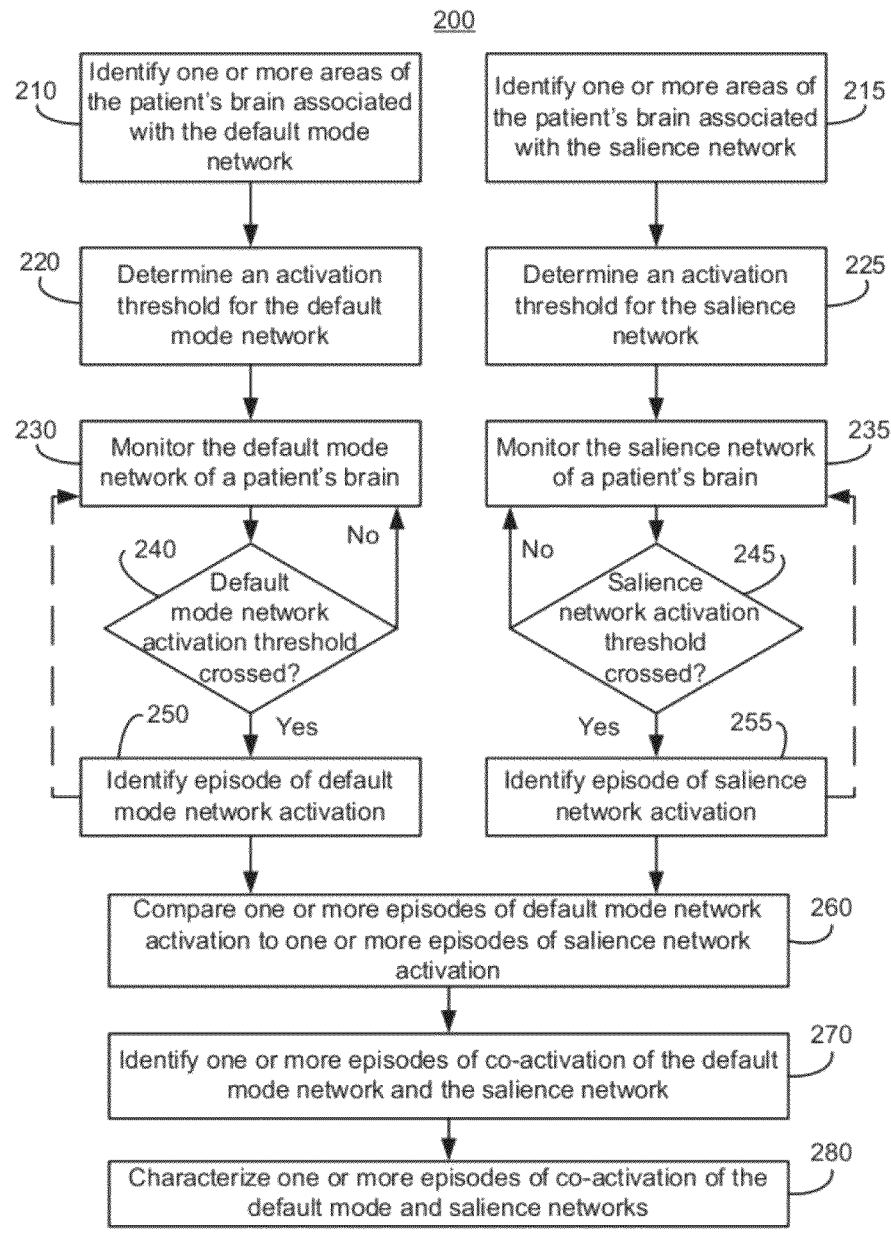
FIG. 2 is a flow diagram demonstrating various aspects of identifying episodes of network co-activation.

FIG. 2 illustrates a flow chart of a method 200 for identifying network brain areas and characterizing co-activation episodes. The default mode network and salience network are currently understood functionally because the brain areas associated with these functions vary from patient to patient. However, the brain areas respectively associated with these functions can be identified (210 and 215) for use in identifying co-activation episodes of a particular patient. Various techniques can be used for identification (210 and 215) of these areas. For example, a patient can be placed within an fMRI (functional magnetic resonance imagining) field. fMRI can map brain activity to a 2D or 3D plot (e.g., on a computer display) allowing activated brain areas to be identified, usually indicated by being colored or otherwise highlighted. While fMRI is used as an exemplar in this disclosure, all other types of neural imaging are contemplated to be used in the same way, including magnetoencephalogram (MEG) and positron emission tomography (PET).

A brain area is activated, as referred to herein, when organized neural activity of that brain area increases beyond a dormant state. An image produced by an fMRI can indicate which brain areas have increased blood flow and energy (glucose) consumption, which is indicative of increased neuron firing (in frequency and/or number). Therefore, one or more areas of the patient's brain associated with the default mode network or the salience network can be identified 210 by getting the patient into a state of mind that is likely to activate the areas of the brain in support of the function in interest (e.g., default mode network or salience network).

For example, a patient in an fMRI field can be asked to clear his or her mind and not think of anything in particular in an attempt to get the patient into a state of mind which should activate the default mode network and be identifiable via fMRI. Or a patient can be placed in the fMRI field waiting for an extended period (with the aim of having the mind of the patient wander off) and then can be asked to report what he or she was thinking about at certain times. The times for which the patient reported not having a discernable thought (or some other state of mind associated with the default mode network) can then be identified and the brain activation patterns of those times studied. One or more areas of the brain activated during one or more periods of non-thinking as indicated by the fMRI plot can then be identified 210 as the one or more areas of the patient's brain associated with the default mode network function. It will be understood that a default mode network pattern may emerge with one fMRI image of one instance of default mode network-type of thinking for some patients. However, many episodes and images may be used to recognize activation patterns and map areas of the brain to default mode network function for identification 210 for a patient as needed.

One or more areas of the patient's brain associated with the salience network can be identified 215 by a similar technique as identification 210 of default network brain areas. Identification 215 can include giving cognitive or movement tasks to the patient while he or she is in the fMRI field, such as asking the patient to count backwards, move his or her hand in a particular way, or to play with a puzzle. The cognitive or movement tasks can be designed to challenge the function of the salience network. Concurrent with the patient's performance of these tasks, fMRI data can be collected to see which one or more brain areas are activated in response to performance of the tasks, which in some cases are likely to be the brain areas that support the salience network.

There are various techniques that can be used to control for the state of mind the patient is in when collecting data. For example, a patient's state of mind can be controlled through suggestion in a clinical environment and/or a patient can self report as to his or her state of mind by immediately reporting this to a clinician, keeping a journal, or by entries into an electronic data collection device that time stamps the sensed data and entries for later comparison. In various embodiments, a device or clinician may recognize that some brain activity is suspected to be default mode or salience network activation and then the patient can be queried by the device or clinician as to his or her state of mind. In various embodiments, a patient might hit a button or perform some other input when he or she recognizes that he or she has just had a cognitive issue. Following the input, the device can then store the recently sensed data or start collecting data.

The method 200 includes determining 220 an activation threshold for the default mode network. The activation threshold can be determined 220 based on the same data used to identify 210 the brain areas associated with default mode network function. For example, while looking to see which brain area(s) are being activated when the patient is thought to be in a state of mind associated with default mode network function, the level of increase in brain activity those area(s)

exhibited can be analyzed. In some cases, an electrode can collect a bioelectrical signal from the brain and a part of the signal can be analyzed based on activation of a particular brain area (e.g., default mode network) as determined by fMRI, patient self-reporting, or the timing of a suggestion to the patient. The bioelectrical signal may be converted to the frequency domain and a power level of a particular frequency, such as a beta or gamma band frequency, can increase at the same time that the fMRI detected the network activation or for the same time the patient reported a particular state of mind. Changes in bioelectrical signal amplitude and phase are also possible. The changes in the bioelectrical signal may be noted and an activation threshold may be determined 220 and 225 based on the bioelectrical signal change, such as a frequency domain power level change for a particular frequency or a signal amplitude change. Subsequent changes in the bioelectrical signal that crosses the threshold can mark activation of the identified 210 and 215 networks. As such, in some embodiments, determining 220 and 225 activation thresholds can represent transition from initial imaging-based identification 210 and 215 of networks to chronic monitoring based on bioelectrical brain signals. It is noted that different thresholds will preferably be determined 220 and 225 for each of the default mode and salience networks.

Determining 220 and 225 an activation threshold can be useful when a brain area thought to be associated with a type of function (e.g., default mode network) normally has some level of brain function even when the state of mind associated with the type of function is clearly not present. However, the brain area may then have a large increase in activity when the patient is thought to be in the state of mind associated with the brain state in question. The increase may be quantized (e.g., percent neural activation) and then a point selected within the increase. For example, if a certain area identified 210 to be associated with default mode network activation is at 10% neural activation when the patient is not in a default mode network state of mind, and the activation increases to 40% when the patient is thought to be in a default mode network state of mind, then the default mode network threshold can be set within this range, such as ⅓ (20%) or ¼ (25%) of the range. Activation thresholds for other parameters can likewise be set, such as for amplitude, frequency, frequency band power, and phase of bioelectrical brain signals, among others.

Once the activation threshold for the default mode network has been determined 220, then the default mode network can be monitored 230 by monitoring those areas of the patient's brain (locally or globally) using the determined 220 default mode network activation threshold to detect if the default mode network activation threshold has been crossed 240. If the threshold is crossed 240 then an episode of default mode network activation is identified 250. The method 200 may return to monitoring 230 (as indicated by dashed line), or the method 200 may continually monitor 230 without interruption to log default mode network identification 250.

In some embodiments, certain brain areas identified 210 to be associated with the default mode network are identified 210 with one parameter (e.g., percent activation on fMRI) and monitored 230 using an activation threshold of the same parameter. However, in some other embodiments, certain brain areas are identified 210 to be associated with the default mode network using one parameter (e.g., percent activation on fMRI) and monitored 230 using an activation threshold of a different parameter of a different brain measurement system, such by amplitude or frequency power band of an electrode measuring local field potential (LFP). It may be easier to identify 210 and 215 which areas of the brain are respectively associated with default mode network and salience network activation using fMRI in a clinical setting, and then locate electrodes of an implantable device proximate those areas for chronic monitoring 230 and 235. In this example, activation data from fMRI can be used to determine 220 a LFP activation threshold by correlating an increase in some parameter of the bioelectrical signal with the fMRI activation images, with the activation threshold being set within the increase of the parameter. The activation threshold can be set at the midpoint of the measured increase in the bioelectrical parameter between the parameter value measured when the fMRI indicated no network activation to the parameter value measured at the time when the fMRI indicated network activation. It is noted that the bioelectrical signals that characterize brain network activation are generally expected to be low frequency oscillation patterns, however any other signatures of activation are contemplated for performing the functions described herein.

It will be understood that each of the options discussed herein for steps 210-220-230-240-250 also apply to steps 215-225-235-245-255 in identifying 255 episodes of salience network activation. For example, salience network activation can be monitored 255 based on a salience network activation threshold parameter that is of a different type than the type of parameter used to identify 215 the one or more brain areas associated with salience network activation. It will also be understood that steps 210-220-230-240-250 (or an equivalent for identifying activation of a particular network) may be essentially identical to steps 215-225-235-245-255 (or an equivalent for identifying activation of a different network), but for the type of activation targeted (e.g., default mode network vs. salience network). It will also be understood that steps 210-220-230-240-250 (or an equivalent for identifying default mode network activation) may be different from steps 215-225-235-245-255 (or an equivalent for identifying salience network activation), the difference being more than the type of activation targeted. For example, the salience network may be monitored 235 using fMRI while the default mode network may be monitored 230 using one or more bioelectrical signals (e.g., LFP or EEG). The same or different technique for determining 220 a default mode network activation threshold, monitoring 230 a patient's default mode network, checking whether the default mode network threshold is crossed 240, and identifying 250 default mode network activation based on the default mode network threshold being crossed 240, can be used in determining 225 a salience network activation threshold, monitoring 235 a patient's salience network, checking whether the salience network threshold is crossed 245, and identifying 255 salience network activation based on the salience network threshold being crossed 245.

The method 200 includes comparing 260 one or more identified 250 episodes of default mode network activation to one or more identified 255 episodes of salience network activation. Such a comparison may take several forms. For example, the activation episodes of the different networks may be compared temporally. Temporal comparison may determine if episodes of different networks temporally overlap in whole or in part. Temporal comparison may also determine the duration of overlap of the episodes of the different networks. Various embodiments may determine what percentage of a type of activation comprises co-activation (e.g., total time of co-activation divided by the total time of only default mode activation or alternatively only salience network activation) which can provide a measure of proper brain activity verses improper brain function. Various other metrics are discussed elsewhere herein and are contemplated as useful for comparing 260 and identifying 270 co-activation episodes, such as frequency, amplitude, and phase.

Based on the comparison 260, one or more episodes of co-activation of the default mode network and the salience network may be identified 270. As discussed herein, one or more criteria may be used to identify 270 network co-activation. For example, in some embodiments, if a default mode network parameter being monitored 230 is above a default mode network activation threshold while a salience network parameter being monitored 235 is likewise above a salience network activation threshold, then co-activation of the networks may be identified 270. However, various embodiments may require more than simultaneous activity, and may further require matching of the bioelectrical oscillations in the respective networks (e.g., both networks having the same phase or frequency of bioelectrical oscillation) to identify 270 a co-activation episode. Various other criteria referenced herein can be used in any combination in various embodiments, such that an episode of co-activation is identified based on correspondence between one, two, three, or more different criteria.

The method 200 further includes characterizing 280 the one or more episodes of co-activation of the default mode and salience networks. Such characterization 280 may include determining the degree of correspondence between activity of the default mode network and the salience network. Metrics of correspondence may include the degree of match between the bioelectrical amplitude, phase or period of bioelectrical oscillation, and/or frequency of bioelectrical oscillation between activity of the default mode network and the salience network within one or more identified 270 co-activation episodes. Characterizing 280 may include determining the duration of one co-activation episode, counting of episodes over time period of time, and/or determining total time over a period of time that the patient's brain is in a state of co-activation (e.g., minutes per day). An output of a device can be made based on identifying 270 one or more episodes of co-activation and/or characterizing 280 the one or more episodes, such as an indication made on a display.

Various embodiments may determine the overlap in bioelectrical frequency of oscillation between the default mode and salience networks when both networks are activated, which can be a measure of the degree or intensity of co-activation. As such, simultaneous activity in both networks is one indicator of improper brain function while having low frequency oscillations in each of the two networks that match (or are close to matching) in terms of frequency, phase, or period of oscillation is a further indicator of improper brain function, the later indicating a particularly intense episode of co-activation. In various embodiments, simultaneous activity in the default mode network and the salience network alone may not be enough to qualify for co-activation indication. In such embodiments, a further criterion may need to be satisfied, such as frequency matching between the oscillatory brain signals of the two networks. For example, electrical activity of the default mode network and the salience network of a patient may need to oscillate at the same frequency, or close frequencies (e.g., within a predetermined frequency range, such as 5 Hz) for co-activation to be identified 270. In addition or as an alternative to frequency matching, bioelectrical amplitude matching (e.g., networks having comparable increases in amplitude when activated) and/or phase locking (i.e. having consistency in phase between the bioelectrical oscillations of the two networks) may also be used to identify 270 co-activation and/or characterize 280 co-activation, which in the later case may indicate episode intensity.

Various embodiments of the present disclosure concern characterizing the type of co-activation. For example, the temporal co-activation of default mode and salience networks may be a fading overlap, where one network is ramping up and the other is ramping down, but ramping up too quickly and/ramping down too slowly such that the two networks are deemed to be activated during the ramping phases. If this is the case, it may be determined that the brain is trying to balance the default mode and salience networks, but is slow to do so. Alternatively, if it is determined that the temporal overlap is not correlated with ramping phases (e.g., in sustained co-activation), then it may be determined that the brain is not attempting to balance the networks, or is unable to balance the networks. As such, a distinction can be made in characterizing co-activation between ramping co-activation and sustained co-activation.

Identifying an episode of default mode network or salience network activation may include determining the duration of the episode. The duration of an episode may be measured from the time the monitored parameter rises above an activation threshold to the time that it falls below the activation threshold. The duration of an episode of co-activation may then be the period during which both of the monitored default mode network parameter and the monitored salience network parameter were first above respective activation thresholds to the time that one of the parameters fell below respective thresholds.

In various embodiments, activation of one or more brain area(s) associated with default mode network function is detected not merely by electrical activity in that area of the brain, but the electrical activity exhibiting a particular pattern. For example, significant electrical activity in a certain area of the brain associated with default mode network function may be present, but activation of the default mode network is not recognized until activity in a certain frequency band increases to a threshold level (e.g., detected by comparing the power level of bioelectrical oscillation at a particular frequency to a threshold). Identification of salience network activation may similarly require recognition of a certain pattern to be considered to be in an activated state.

Different frequency bands are associated with different activities in the brain. Generally accepted frequency bands are shown in Table 1:

TABLE 1

| Frequency (f) Band Hertz (Hz) | Frequency Information |
| --- | --- |
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

While some techniques discussed herein determine activation of a network by comparison to static information (e.g., a threshold), not all embodiments are so limited. In various embodiments, recognition of a similarity between activity of the default mode network and the salience network is used to identify an episode of co-activation of these networks, where just one of the networks exhibiting the same activity alone would not be recognized as activation of that particular network. For example, a processor of control circuitry may compare frequency band characteristics of a first signal (e.g., power level) associated with the default mode network to frequency band characteristics of a second signal associated with the salience network to determine whether the two signals exhibit substantially common frequencies or some other characteristic during the same period. In various embodiments, if the processor determines that the power levels of particular frequencies of the first and second signals are substantially similar (e.g., are within a threshold amount of each other), then the processor may detect activation of both networks. In various embodiments, if the processor determines that the greatest power levels of the two signals within a common frequency band are associated with the same frequencies (e.g., are within a threshold amount of each other), then the processor may detect activation of both networks. As such, co-activation of networks may be identified based on recognition of a commonality exhibited by both networks simultaneously, such as phase locking of oscillations between the networks or having the same dominant frequency of bioelectrical oscillation.

It is noted that a healthy person may still have occasional periods of default mode network and salience network co-activation. In such cases, the co-activation is short lived and infrequent. For example, co-activation may occasionally occur when one of the networks is ramping up and the other is ramping down. As such, various embodiments concern identifying repeated co-activation episodes and tracking co-activation episodes to determine whether the episodes are becoming more frequent (e.g., episodes per hour, day, week), longer, and/or more intense (e.g., electrical activity of one network at a higher amplitude and/or closer frequency matching between bioelectrical oscillations of the networks). Also, the use of a minimum co-activation duration threshold may be used to qualify an episode of co-activation for identification, tracking of a condition, and/or controlling a therapy. For example, an occurrence of co-activation may not count as co-activation for the purpose of identifying an episode of co-activation, tracking a condition, and/or controlling a therapy until the co-activation episode persists for a predetermined period of time (e.g., 1 minute).

In various embodiments, a threshold or other criteria for identifying activation of a network is not static, and may change based on various conditions. For example, threshold criteria for detecting activation of the default mode network based on, for example, a bioelectrical brain signal, may change based on the activity of the salience network. Because the default mode and salience networks can work antagonistically with each other, the higher activity in one network may lower the threshold for detecting activation of the other network. For example, if the electrical activity of the default mode network is relatively high, where it would be expected for a healthy individual that the electrical activity of the salience network would be relatively low during this time, then the threshold for identifying activation of the salience network can be lowered relative to the threshold level it would be at if the default mode network was currently less active. As such, the criteria (e.g., threshold) for identifying activation of the networks can be dynamically changed based on the activity of the other of the networks. In some embodiments, only the default mode network activation threshold is changed, while in some other embodiments only the salience network activation threshold is changed, however both thresholds can be changed in some other implementations.

Various embodiments of the present disclosure concern delivering or otherwise guiding a therapy based on network co-activation. The therapy may address the brain condition underlying co-activation. The therapy may address Alzheimer's disease, for example. The therapy may attempt to correct brain function by minimizing co-activation of default mode and salience networks. The therapy may attempt to improve the patient's condition despite co-activation, such as by supporting other areas of the brain, or otherwise treating the symptoms associated with inappropriate co-activation.

In various embodiments, a drug therapy may be administered based on identification of co-activation of default mode and salience networks. In various embodiments, an electrical simulation therapy is delivered to the patient to address the brain condition. Various different electrical stimulation therapies can address the brain condition in different ways. One type of electrical stimulation therapy concerns network suppression.

Network suppression may include stimulating to prevent or stop activation of one or both networks. In some embodiments, network suppression may stimulate to disrupt matching of oscillations of neurons within a network or between the default mode and salience networks. Such stimulation may prohibit phase locking of bioelectrical oscillations needed for robust activation of a network, such as the default mode network, or stop bioelectrical oscillations of a particular frequency. In suppression therapy, electrical stimulation is delivered to one or more areas of the brain to suppress activation of one or both of the default mode network and the salience network. Such suppression may occur prophylactically in an attempt to suppress a network (e.g., the default mode network) before the next episode of co-activation begins. Additionally, or alternatively, the electrical stimulation can be delivered to one or more areas of the brain to suppress one or both of default mode network and salience network activation when co-activation is occurring. For example, suppressive stimulation can be delivered to suppress the default mode network when co-activation of the default mode and salience networks is recognized. Suppressive stimulation can be delivered to suppress the default mode network when it appears that the salience network is ramping up in activity, but before it is fully activated. Various therapies may alternatively or additionally deliver suppressive stimulation to suppress the default mode network when the salience network is indicated to be activated, regardless of whether co-activation of the default mode and salience networks is indicated. In various embodiments, suppressive stimulation comprises the delivery of high frequency pulses, e.g., 100-1000 HZ or 80-140 HZ, or pulses that attempt a phase reset of a network.

Electrical stimulation referenced herein may suppress a network of a patient's brain to inhibit default mode network and salience network co-activation. Inhibiting co-activation may correct brain function and improve cognitive function, such as by activating the memory and/or cognitive systems of the brain. For example, with patients for whose neurological disorder is characterized by an inability to acquire new memories, reduction of co-activation may allow each of the default mode network and salience network to carry out their respective functions in supporting memory.

In various embodiments, supportive stimulation is delivered. Supportive stimulation can support activation of a brain area. For example, pulses can be delivered in the beta or gamma frequency ranges to cause a network to activate. In various embodiments, supportive stimulation is delivered during co-activation to help one of the networks, such as the salience network, persist or increase in activation strength. In various embodiments, when co-activation is detected, one of the salience and default mode networks can be stimulated with supportive stimulation while the other of the salience and default mode networks is stimulated with suppressive stimulation. In some embodiments, a preference can be established, such as for the activation of the salience network, such that when co-activation is detected the salience network can be stimulated with supportive stimulation and the default mode network can be stimulated with suppressive stimulation. However, it some embodiments, the default mode network is stimulated with supportive stimulation and the salience network is stimulated with suppressive stimulation when co-activation is detected.

In various embodiments, a therapy may be delivered on demand based on a patient or clinician control. Therapy may be initiated in this way when the patient and/or clinician thinks that an abnormal brain condition is presently manifesting. For example, a patient may feel that he or she is having a particularly hard time concentrating or remembering, and press a button or otherwise provide an input to trigger the delivery of therapy. A therapy, such as an electrical stimulation therapy to suppress the default mode network, can then be delivered. Alternatively, a device may start a monitoring session upon reception of the input to determine whether co-activation is present based on the input from the patient, and only if co-activation is recognized by the device is the therapy then delivered.

Figure 3:
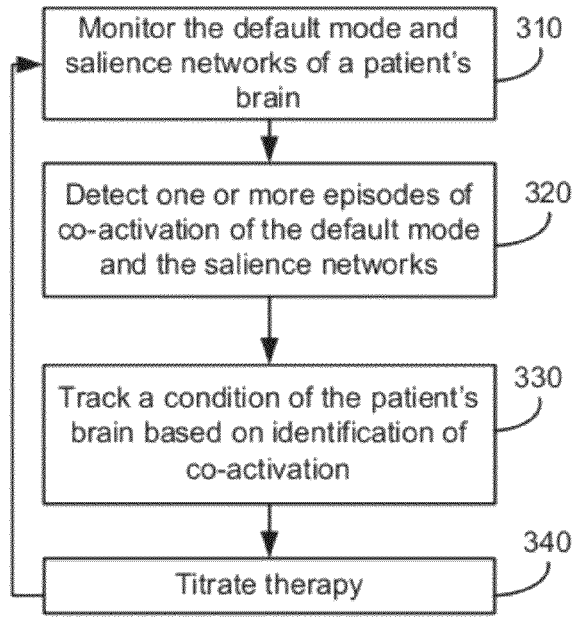
FIG. 3 is a flow diagram demonstrating various aspects of titrating a therapy based on network co-activation.
Figure 4:
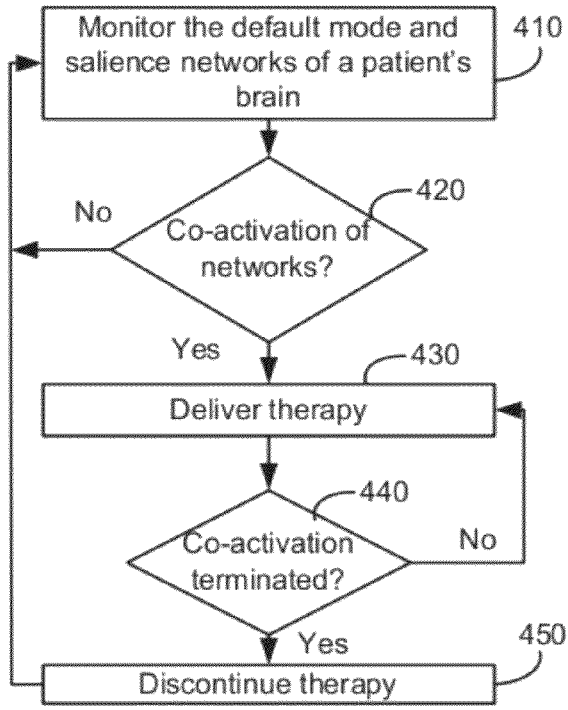
FIG. 4 is a flow diagram demonstrating various aspects of controlling a therapy based on network co-activation.

FIGS. 3 and 4 illustrate flow charts of methods 300 and 400 for controlling therapy based on network co-activation. The method 300 of FIG. 3 includes monitoring 310 the default mode and salience networks of a patient's brain. Such monitoring 310 can be performed according to any technique referenced herein, and can be proceeded by the identification of the brain areas and determination of activation thresholds, as in the method 200 of FIG. 2, for example. The method 300 can further include detecting 320 one or more episodes of co-activation of the default mode and the salience networks. Such detection can be done according to any technique disclosed herein, and can include characterization of the one or more episodes of co-activation. Based on the one or more detected 320 episodes of co-activation, a condition of the patient's brain may be tracked 330. Tracking 330 may include determining worsening or improving of the brain condition based respectively on increasing or decreasing frequency, duration, and/or intensity of the co-activation episodes. As such, tracking 330 may include comparing one or more recently detected 320 episodes of co-activation to less recently detected 320 episodes of co-activation to recognize a change over time in the co-activation episodes. Therapy can be titrated 340 based on the tracking 330 of the condition. For example, if the tracking 330 indicates a worsening brain condition, then the therapy may be started, or increased. In the case of a drug therapy, titration 340 may include prescription of a drug for delivery, delivery of a drug (e.g., by an implantable drug pump), and/or an increase in administration of a drug (e.g., increasing the amount or concentration) if the condition is tracked 330 to be worsening, and the drug delivery may be stopped or tapered if the condition is tracked 330 to be improving. In the case of an electrical stimulation therapy to suppress or support a brain network, the electrical stimulation therapy may be started or increased in frequency, amplitude, and/or duration if the condition is tracked 330 to be worsening, and the electrical stimulation therapy may be stopped or decreased in frequency, amplitude, and/or duration if the condition is tracked 330 to be improving. As such, a therapy addressing a brain condition, such as Alzheimer's disease, can be titrated 340 based on one or more episodes of default mode network and salience network co-activation.

Therapy titration 340 may include evaluating therapy effectiveness and adjusting the intensity, frequency, duration, or type of therapy delivery. Titration 340 may include discriminating therapy responders from non-responders and changing therapy accordingly, such as stopping therapy and/or switching to a different type of therapy altogether.

FIG. 4 illustrates a method 400 of control of a therapy that addresses a brain condition, such as Alzheimer's disease. The method 400 includes monitoring 410 the default mode and salience networks of a patient's brain, which can be done according to any technique referenced herein. A check 420 is performed to determine if the networks are co-activating. If co-activation is not detected, periodic or continuous monitoring 410 continues, as indicated by the "no" branch. However, if co-activation is detected at the check 420, then therapy is delivered 430 (e.g., suppressive and/or supportive electrical stimulation) until the co-activation is found to be terminated at check 440. Checks 420 and 440 can be performed in any manner referenced herein, including determining whether a network threshold is crossed, the threshold indicative of network activation. Therapy delivery 430 may include delivering a drug through an implanted drug pump or electrical stimulation to the default mode network, although the other targets and modes of delivery as discussed herein could additionally or alternatively be used. As such, various embodiments of the present disclosure concern real-time monitoring, identification, and delivery of therapy to address co-activation of the default mode and salience networks.

In various embodiments, electrical therapy is delivered directly to a targeted area by locating an electrode within that targeted area and using the electrode as an cathode or anode during delivery of electrical energy, such as in the form of one or more pulses. The targeted area may be the one or more areas identified 210 as being associated with the default mode network or identified 215 as being associated with the salience network. The targeted areas could be the brain tissues that directly support the default mode and/or salience networks.

In some cases it may be preferable to directly stimulate an associated brain area (e.g., remote from the default mode network) in an effort to bring about a change in a targeted area (e.g., the default mode network). In such cases, the targeted area may be electrically "down stream" from the associated brain area, such that it is more effective and/or safer to electrically treat the targeted area remotely than directly. Stimulation delivered to the associated portion of the brain, rather than directly to the targeted portion, may have broader outputs to larger areas of the brain outside and including the targeted portion of the brain. In some examples, the targeted portion of the brain may be a more posterior region than the associated portion of the brain, such that electrical stimulation of the associated portion activates a relatively larger area within the brain of the patient than electrical stimulation of the targeted portion directly.

Figure 5:
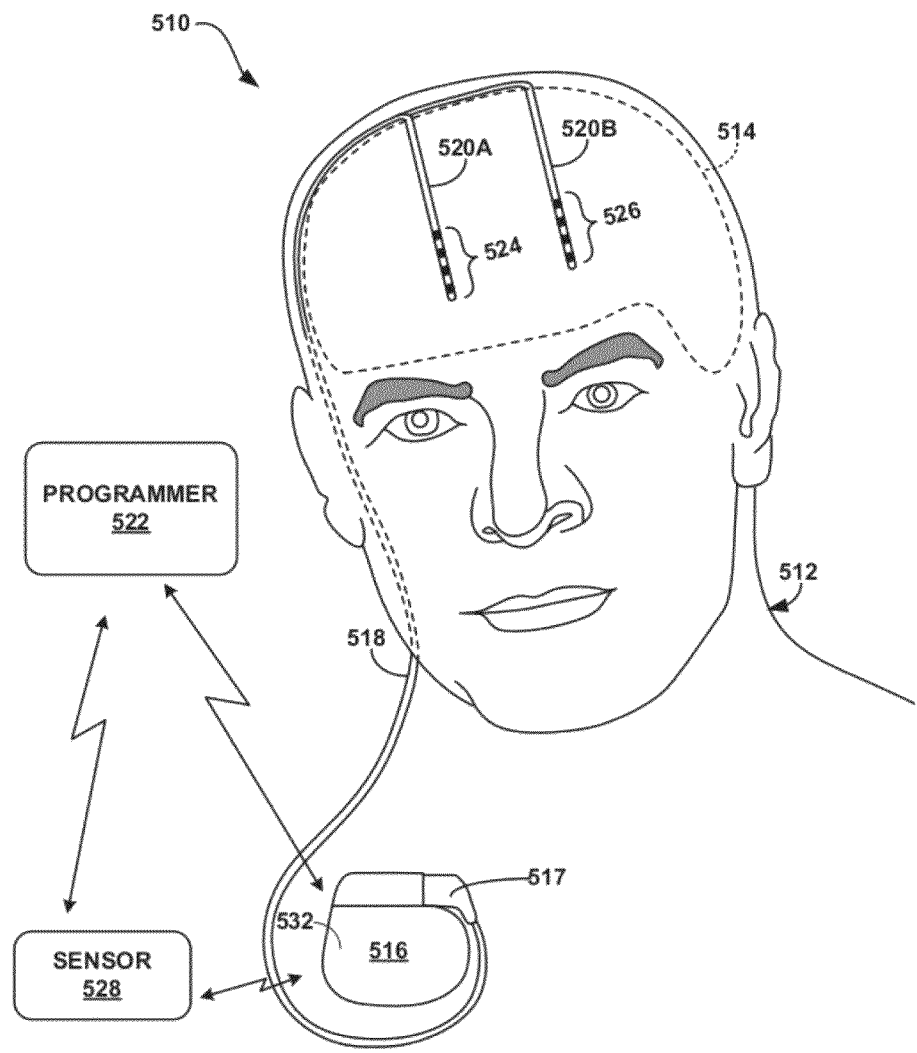
FIG. 5 is a conceptual diagram illustrating an example system that monitors network activation and/or delivers therapy to a patient to manage a disorder of the patient.

FIG. 5 is a conceptual diagram illustrating an example therapy system 510 that monitors a brain condition and/or delivers therapy to patient 512 to manage the brain condition of patient 512. System 510 includes implantable medical device (IMD) 516, lead extension 518, one or more leads 520A and 520B (collectively "leads 520") with respective sets of electrodes 524, 526, medical device programmer 522, and sensor 528, which may be external to patient 512 or implanted within patient 512. IMD 516 may include a module including monitoring circuitry that senses electrical brain signals and identifies brain activity and conditions via the electrodes 524, 526 of leads 520A and 520B, respectively.

System 510 may monitor one or more bioelectrical brain signals of patient 512. For example, IMD 516 may include a sensing module (e.g., sensing module 544 of FIG. 6) that senses bioelectrical brain signals within one or more regions of brain 514. In the embodiment shown in FIG. 5, the signals may be sensed by electrodes 524, 526 and conducted to the sensing module within IMD 516 via conductors within the respective lead 520A, 520B. As described in further detail below, in some examples, a processor, as part of control circuitry of IMD 516 or another device (e.g., programmer 522), monitors the bioelectrical signals within brain 514 of patient 512 to identify network activation, recognize co-activation, characterize co-activation episodes, and/or performs the other functions referenced herein including those of FIGS. 1-4. A processor of IMD 516 or another device (e.g., programmer 522) as part of control circuitry may control delivery of an electrical stimulation or drug therapy to brain 514 based on the identification of co-activation in a manner to treat a brain condition of patient 512.

In some examples, the sensing module of IMD 516 may receive the bioelectrical signals from electrodes 524, 526 or other electrodes positioned to monitor bioelectrical brain signals of patient 512 (e.g., if housing 532 of IMD 516 is implanted in brain 514, an electrode of housing 532 can be used to sense bioelectrical brain signals and/or deliver stimulation to brain 514). Electrodes 524, 526 may also be used to deliver electrical stimulation from the therapy module to target sites within brain 514 as well as to sense brain signals within brain 514. However, IMD 516 can also use separate sensing electrodes to sense the bioelectrical brain signals. In some examples, the sensing module of IMD 516 may sense bioelectrical brain signals via one or more of the electrodes 524, 526 that are also used to deliver electrical stimulation to brain 514. In other examples, one or more of electrodes 524, 526 may be used to sense bioelectrical brain signals while one or more different electrodes 524, 526 may be used to deliver electrical stimulation.

The bioelectrical brain signals monitored by IMD 516 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LH) sensed from within one or more regions of brain 514, and/or action potentials from single cells within the brain 514 of one or more networks. These and other signals can be used to perform the various functions referenced herein, including detection of network activation.

As discussed herein, the monitored brain signals of patient 512 may be used to monitor activation of the default mode and salience networks of brain 514. Metrics that can be used to detect network activation and further characterize episodes of co-activation include time domain characteristics (e.g., an amplitude, frequency, or phase) or frequency domain characteristics (e.g., an energy level in one or more frequency bands as measured by power) of the brain signals sensed by IMD 516 within one or more regions of brain 514. For example, the characteristic of the brain signals may include an absolute amplitude value or a root mean square amplitude value. In addition, the amplitude value may comprise an average, peak, mean or instantaneous amplitude value over a period of time or a maximum amplitude or an amplitude in a particular percentile of the maximum (e.g., an amplitude value that represents 95% of the maximum amplitude value).

As another example, the characteristic of the brain signal may include the frequency amplitude, and phase of the bioelectrical brain signal sensed within one or more regions of brain 514 of patient 512 associated with one of the default mode and salience networks. The frequency; amplitude, and phase of the bioelectrical brain signal may indicate the oscillations in the brain signal and be used to determine when a network is activated. The oscillations in the sensed bioelectrical brain signal may represent the rhythmic or repetitive neural activity in brain 514 when a particular network is activated to perform a particular function, such as the functions associated with the default mode network and the salience network. The neural oscillations may be determined based on one or more frequency domain characteristics of the bioelectrical brain signal.

In some examples, as illustrated in FIG. 5, system 510 may also include sensor 528. In addition to electrodes 524, 526, sensor 528 may measure a physiological response of patient 512 that can be indicative of a particular state of mind of the patient. For example, sensor 528 may be an accelerometer configured to measure movement of the patient which can be indicative of active and conscious thought as the patient purposefully navigates and moves about. The sensor 528 can be an electromyogram (EMG) signal indicative of skeletal muscle movement and therefore patient actions or movement. Such a sensor 528 can be useful in detecting and/or confirming salience network activation or proper brain function, among other things. The sensor 528 may detect other parameters indicative of network activation, such as speech (the sensor 528 being a microphone or sensitive accelerometer) which is further indicative of salience network activation. Sensor 528 may be external to patient 512 and may communicate with IMD 516 and/or programmer 522 via a wireless communication link. In various embodiments, sensor 528 may be implanted within patient 512 and may communicate with IMD 516 via a wired or wireless communication link, and communicate with programmer 522 via a wireless communication link. In embodiments in which sensor 528 is implanted in patient 512, sensor 528 may be physically separate from IMD 516 or may be incorporated in IMD 516.

As described in further detail below, in the examples described herein, IMD 516 may deliver therapy to any suitable portion of brain 514 that may play a role in affecting co-activation of the default mode and salience networks, including inhibiting the default mode network to inhibit co-activation of the networks and/or supporting the salience network and/or inhibiting the salience network to inhibit co-activation of the networks and/or supporting the default mode network. In some embodiments, system 510 may deliver therapy to patient 512 to manage a neurological disorder of patient 512. For example, system 510 may provide therapy to correct a brain disorder and/or manage symptoms of a neurodegenerative brain condition. In some embodiments, system 510 may provide therapy to patient 512 to manage Alzheimer's disease. Patient 512 ordinarily will be a human patient. In some cases, however, system 510 may be applied to other mammalian or non-mammalian non-human patients. While examples of the disclosure are described with regard to tracking and treatment of a cognitive disorder such as Alzheimer's disease, in other cases, system 510 may track and/or provide therapy to manage symptoms of other patient conditions.

IMD 516 may include a module that includes a stimulation generator that generates and delivers electrical stimulation therapy to one or more regions of brain 514 of patient 512 via the electrodes 524, 526 of leads 520A and 520B, respectively, in the example shown in FIG. 5, system 510 may be referred to as deep brain stimulation system because IMD 516 may provide electrical stimulation therapy directly to tissue within brain 514, e.g., a tissue site under the dura mater of brain 514. In other embodiments, leads 520 may be positioned to sense brain activity and/or deliver therapy to a surface of brain 514, such as the cortical surface of brain 514.

In the example shown in FIG. 5, IMD 516 may be implanted within a subcutaneous pocket below the clavicle of patient 512. In other embodiments, IMD 516 may be implanted within other regions of patient 512, such as a subcutaneous pocket in the abdomen or buttocks of patient 512 or proximate the cranium of patient 512. Implanted lead extension 518 is coupled to IMD 516 via a connector block (also referred to as a header), which may include, for example, electrical contacts that electrically couple to respective electrical contacts on lead extension 518. The electrical contacts electrically couple the electrodes 524, 526 carried by leads 520 to IMD 516. Lead extension 518 traverses from the implant site of IMD 516 within a chest cavity of patient 512, along the neck of patient 512 and through the cranium of patient 512 to access brain 514. Generally, IMD 516 is constructed of a biocompatible material that resists corrosion and degradation from bodily fluids. IMD 516 may comprise a hermetic housing 532 to substantially enclose control circuitry. In various embodiments, IMD 516 may be implanted only in the head of the patient (e.g., under the scalp) and not in the chest and neck regions.

Electrical stimulation may be delivered to one or more regions of brain 514, which may be selected based on many factors, such as the type of patient condition for which system 510 is implemented to manage. In some examples, leads 520 may be implanted within the right and left hemispheres of brain 514 (e.g., as illustrated in FIG. 5) while, in other examples, both of leads 520 may be implanted within one of the right or left hemispheres. Other implant sites for leads 520 and MD 516 are contemplated. For example, in some examples, IMD 516 may be implanted on or within cranium. In addition, in some examples, a single lead may be implanted within the brain 514.

Leads 520 may be positioned to deliver electrical stimulation to one or more target tissue sites within brain 514 to manage patient symptoms associated with a disorder of patient 512 and/or to preferentially sense bioelectrical signals of the targeted brain areas. Targeted tissues may be the tissues identified 210 and 215 as being associated with the networks in interest, as in the method 200 of FIG. 2. Leads 520 may be implanted to position electrodes 524, 526 at desired locations of brain 514 through respective holes in cranium. Leads 520 may be placed at any location within brain 514 such that electrodes 524, 526 are capable of providing electrical stimulation to target tissue sites within brain 514 during treatment and/or sensing bioelectrical signals of interest, such as those indicative of co-activation. In some embodiments, leads may be placed such that electrodes 524, 526 directly contact or are otherwise proximate targeted tissue of a particular network.

In the example shown in FIG. 5, electrodes 524, 526 of leads 520 are shown as ring electrodes. Ring electrodes may be relatively easy to program and are typically capable of sensing and/or delivering an electrical field to any tissue adjacent to leads 520 (e.g., in all directions away from an outer perimeter of leads 520). In other examples, electrodes 524, 526 of leads 520 may have different configurations. For example, electrodes 524, 526 of leads 520 may have a complex electrode array geometry that is capable of producing shaped electrical fields. The complex electrode array geometry may include multiple electrodes (e.g., partial ring or segmented electrodes) around the perimeter of each lead 520, rather than a ring electrode. In this manner, bioelectrical sensing and/or electrical stimulation may be associated with a specific direction from leads 520 (e.g., in a direction less than around the entire outer perimeter of leads 520) to enhance directional sensing and/or therapy efficacy and reduce possible adverse side effects from stimulating a large volume of tissue in the case of stimulation. As such, electrodes can be positioned to stimulate targeted tissue (e.g., the tissue of the default mode network or the salience network) and avoid stimulating non-targeted tissue.

In some embodiments, outer housing 532 of IMD 516 may include one or more stimulation and/or sensing electrodes. For example, housing 532 can comprise an electrically conductive material that is exposed to tissue of patient 512 when IMD 516 is implanted in patient 512, or an electrode can be attached to housing 532. In alternative examples, leads 520 may have shapes other than elongated cylinders as shown in FIG. 5. For example, leads 520 may be paddle leads, spherical leads, bendable leads, or any other type of shape effective in treating patient 512.

In some examples, the location of the electrodes 524, 526 within brain 514 can be determined based on analysis of a bioelectrical brain signal of the patient sensed via one or more of the electrodes 524, 526. For example, a particular physiological structure may exhibit a bioelectrical signal (e.g., indicative of the default mode network or the salience network), thus facilitate positioning of the electrodes of the lead at the desired implant location (e.g., near the target tissue) through monitoring of the bioelectrical signal.

Stimulation generator 542, under the control of processor 540 as part of control circuitry, generates stimulation signals for delivery to patient 512 via selected combinations of electrodes 524, 526. Processor 540 controls stimulation generator 542 according to stimulation programs 552 stored in memory 541 as part of control circuitry to apply particular stimulation parameter values specified by one or more programs, such as amplitude, pulse width, and pulse rate. In some examples, stimulation generator 542 generates and delivers stimulation signals to one or more target portions of brain 514.

Leads 520 may be implanted within a desired location of brain 514 via any suitable technique, such as through respective burr holes in a skull of patient 512 or through a common burr hole in the cranium. Leads 520 may be placed at any location within brain 514 such that electrodes 524, 526 of leads 520 are capable of sensing electrical activity of the networks of interest (e.g., default mode and salience networks) and/or providing electrical stimulation to targeted tissue for treatment (e.g., to stimulate one or both of the default mode and salience networks).

In some examples, a processor of system 510 (e.g., a processor of programmer 522 or MD 516) controls delivery of electrical stimulation by activating electrical stimulation, deactivating electrical stimulation, increasing the intensity of electrical stimulation, or decreasing the intensity of electrical stimulation delivered to brain 514 based on the identification of one or more episodes of co-activation of default mode and salience networks. Therapy can be started, stopped, and/or changed by processor 540 in any manner and based on any parameter or finding as discussed herein.

System 510 may also store a plurality of stimulation programs (e.g., a set of electrical stimulation parameter values), and at least one stimulation program may be associated with at least one type or degree of co-activation. A processor of IMD 516 or programmer 522 may select a stored stimulation program that defines electrical stimulation parameter values for delivery of electrical stimulation to brain 514 based on a characterization or tracking of a brain condition based on co-activation. Where IMD 516 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities.

External programmer 522 wirelessly communicates with IMD 516 as needed to provide or retrieve information. For example, external programmer 522 may receive sensed data and/or information regarding one or more episodes of co-activation from IMD 516, as well as send therapy program information to IMD 516. Programmer 522 is an external computing device that the user, e.g., the clinician and/or patient 512, may use to communicate with IMD 516. For example, programmer 522 may be a clinician programmer that the clinician uses to communicate with IMD 516 and program one or more therapy programs for IMD 516. Additionally or alternatively, programmer 522 may be a patient programmer that allows patient 512 to input an indication of their state of mind (e.g., a self evaluated assessment concerning a clear, confused, blank, or engaged state of mind), select programs, and/or view and modify therapy parameters.

Programmer 522 may be a hand-held computing device with a display viewable by the user and an interface for providing input to programmer 522 (i.e., a user input mechanism). For example, programmer 522 may include a small display screen (e.g., a liquid crystal display (LCD) or a light emitting diode (LED) display) that presents information to the user. In addition, programmer 522 may include a touch screen display, keypad, buttons, a peripheral pointing device or another input mechanism that allows the user to navigate though the user interface of programmer 522 and provide input. The screen (not shown) of programmer 522 may be a touch screen that allows the user to provide input directly to the user interface shown on the display. The user may use a stylus or their finger to provide input to the display.

In other examples, programmer 522 may be a larger workstation or a separate application within another multi-function device, rather than a dedicated computing device. For example, the multi-function device may be a notebook computer, tablet computer, workstation, cellular phone, personal digital assistant or another computing device.

When programmer 522 is configured for use by the clinician, programmer 522 may be used to transmit initial programming information to IMD 516. This initial information may include hardware information, such as the type of leads 520, the arrangement of electrodes 524, 526 on leads 520, the position of leads 520 within brain 514, initial programs defining therapy parameter values, and any other information that may be useful for programming into IMD 516. Programmer 522 may also be capable of completing functional tests (e.g., measuring the impedance of electrodes 524, 526 of leads 520).

The clinician may also store therapy programs within IMD 516 with the aid of programmer 522. During a programming session, the clinician may determine one or more stimulation programs that may effectively bring about a therapeutic outcome that treats a brain condition, such as suppression of the default mode network. For example, the clinician may select one or more electrode combinations with which stimulation is delivered to brain 514 to effectuate the suppression state. During the programming session, the clinician may evaluate the efficacy of the one or more electrode combinations based on one or more findings of an fMRI, patient self reporting, LFP, EEG, or some other parameters for investigating network activation of the patient 512. In some examples, programmer 522 may assist the clinician in the creation/identification of stimulation programs by providing a methodical system for identifying potentially effective stimulation parameter values. In some examples, the processor of programmer 522 may calculate and display one or more therapy metrics for evaluating and comparing therapy programs available to delivery of therapy from IMD 516 to patient.

Programmer 522 may also provide an indication to patient 512 when therapy is being delivered which may aid the assessment of therapy efficacy. For example, upon seeing that therapy is being delivered (e.g., to suppress the default mode network) the patient may evaluate whether he or she seems to have a clearer state of mind and/or is able to perform better on a cognitive and/or memory test administered by programmer 522.

Whether programmer 522 is configured for clinician or patient use, programmer 522 is configured to communicate with IMD 516 and, optionally; another computing device, via wireless communication. Programmer 522, for example, may communicate via wireless communication with IMD 516 using radio frequency (RF) telemetry techniques known in the art. Programmer 522 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 522 may also communicate with other programming or computing devices via exchange of removable media, such as magnetic or optical disks, memory cards or memory sticks. Further, programmer 522 may communicate with IMD 516 and another programmer via remote telemetry techniques known in the art, communicating via a local area network (LAN), wide area network (WAN), public switched telephone network (PSTN), or cellular telephone network, for example.

FIG. 5 is a functional block diagram illustrating, among other things, control circuitry components of IMD 516. In the example shown in FIG. 5, IMD 516 includes processor 540, memory 541, stimulation generator 542, sensing module 544, switch module 546, telemetry module 548, and power source 550. Memory 541 may include any volatile or non-volatile media, such as a random access memory (RAM), read only memory (ROM), non-volatile RAM (NVRAM), electrically erasable programmable ROM (EEPROM), flash memory, and the like. Memory 541 may store computer-readable instructions as part of operating instructions 556 that, when executed by processor 540, cause MID 516 to perform various functions described herein as part of control circuitry.

The steps, procedures, techniques, etc. referenced herein may be carried out in part by, for example, software instructions, such as those used to define a software or computer program. The computer-readable medium can store instructions as part of control circuitry. The computer-readable medium may be a computer-readable storage medium such as a storage device (e.g., a disk drive, or an optical drive), memory (e.g., a Hash memory, random access memory or RAM) or any other type of volatile or non-volatile memory that stores instructions (e.g., in the form of a computer program or other executable) to cause a programmable processor to perform the actions described herein.

Processor 540 may determine whether a sensed bioelectrical brain signal includes a biomarker for a particular network activation (e.g., a particular power level of a particular frequency band indicative of activation of the salience network or the default mode network), processor 540 may analyze a sensed bioelectrical signal amplitude of frequency correlation with a template signal, or a specific stored value. For example, the instantaneous, peak, lowest or average amplitude of the bioelectrical brain signal over a period of time (which can be predetermined) may be compared to an amplitude threshold.

As another technique that can be implemented by processor 540 for activation detection, memory 541 may store portions of bioelectrical brain signals (e.g., waveforms or specific values of signal characteristics) previously sensed within brain 514 of patient 512 that correspond to activation of a particular network, such as a default mode network or salience network activation confirmed by fMRI. In some examples, the stored bioelectrical brain signals can be used as a template to determine whether a particular sensed bioelectrical brain signal is indicative of a particular network activation of brain 514. As an example of a signal processing technique that processor 540 may employ to determine whether the bioelectrical brain signal includes the biomarker associated with a particular network activation, processor 540 may analyze the bioelectrical brain signal with feature correlation, temporal correlation, or frequency correlation with a template signal, or combinations thereof. As another example, a slope of the amplitude of the bioelectrical brain signal over time or timing between inflection points or other critical points in the pattern of the amplitude of the bioelectrical brain signal over time may be compared to trend information stored in memory. A correlation between the inflection points in the amplitude waveform of the bioelectrical brain signal or other critical points and a template may indicate the bioelectrical brain signal includes the biomarker indicative of the activation of a particular one or the default mode or salience networks. Processor 540 as part of control circuitry may implement an algorithm that recognizes a trend of the bioelectrical brain signal that characterizes the bioelectrical signal and recognizes such patterns to detect activation of a network.

As another technique for network activation detection, processor 540 may perform temporal correlation by sampling the waveform generated by a sensed bioelectrical brain signal with a sliding window and comparing the waveform with a template waveform stored in memory that is associated with activation of a particular network (e.g., a default mode network or salience network). For example, processor 540 may perform a correlation analysis by moving a window along a digitized plot of the amplitude waveform of a sensed bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the sensed bioelectrical brain signal over time, or by applying any suitable mathematical correlation algorithm between the sample in the sampling window and a corresponding set of samples stored in the template waveform.

As shown, the set of electrodes 524 of lead 520A includes electrodes 524A, 524B, 524C, and 524D, and the set of electrodes 526 of lead 520B includes electrodes 526A, 526B, 526C, and 526D. Processor 540 may control switch module 546 to apply the stimulation signals generated by stimulation generator 542 to selected combinations of electrodes 524, 526. In particular, switch module 546 may couple stimulation signals to selected conductors within leads 520, which, in turn, deliver the stimulation signals across selected electrodes 524, 526. Switch module 546 may be a switch array, switch matrix, multiplexer, or any other type of switching module configured to selectively couple stimulation energy to selected electrodes 524, 526 and to selectively sense bioelectrical brain signals with selected electrodes 524, 526. Hence, stimulation generator 542 is coupled to electrodes 524, 526 via switch module 546 and conductors within leads 520. In some examples, however, IMD 516 does not include switch module 546.

Sensing module 544 is configured to sense bioelectrical brain signals of patient 512 via a selected subset of electrodes 524, 526, or with one or more electrodes 524, 526 and at least a portion of a conductive outer housing 532 of MID 516, an electrode on an outer housing of IMD 516, or another reference. Processor 540 may control switch module 546 to electrically connect sensing module 544 to selected electrodes 524, 526. In this way, sensing module 544 may selectively sense bioelectrical brain signals with different combinations of electrodes 524, 526 (and/or a reference other than an electrode 524, 526).

In various embodiments, signatures of network activation can be learned to facilitate later recognition of activation of that network, particularly in an automated way by control circuitry of a medical device. For example, a clinician or patient 512 can determine when patient 512 exhibits evidence of a brain state, such as clear thinking (salience network activation), no discernable thought (default mode network activation), or confusion (co-activation) and determines the bioelectrical brain signal or other signal sensed by IMD 516 or another device (e.g., fMRI, PET, MEG, or a temporary monitoring device), or particular changes or stand-out features/characteristics of the signals, that correlate in time to when patient 512 exhibited evidence of the brain state. The exhibition of evidence of one or more of the brain states may be referred to as a brain state episode, where each episode may be associated with the exhibition of the brain state. Episodes that occur in a short range of time (e.g., within a few seconds or otherwise determined by the clinician) may be clustered together to define a common episode. The clinician may determine when patient 512 exhibits one or more symptoms of a particular brain state based on any suitable and reliable information, such as by instructing the patient on how to direct his or her state of mind, observing the patient 512 in the clinic, and/or based on a diary, where the diary catalogs the times at which patient 512 exhibited the symptoms of a brain state.

Clinician or control circuitry, such as processor 540 of IMD 516, or a processor of another device, such as programmer 522, may determine the one or more biomarkers indicative of activation of a particular network based on the bioelectrical brain signal that temporally correlates to the brain state episode. The biomarkers may be selected by the clinician or automatically by a processor, and may be selected as the signal characteristics that distinguish the bioelectrical brain signal sensed during a brain state episode from a bioelectrical brain signal sensed at other times. The biomarker can then serve as an activation threshold or other indicator for subsequent detection of network activation.

Another technique for recognizing activation of a particular network concerns comparison of a signal to a threshold that is associated with activation of the network. For example, processor 540 may monitor bioelectrical brain signals sensed by sensing module 544 in any suitable manner in order to identify activation of a particular network of brain 514. For example, sensing module 544 may directly sense a bioelectrical brain signal, e.g., a UP, via one or more of electrodes 524, 526 at a particular point within a portion of brain 514 that concerns the default mode network or the salience network, and processor 540 may monitor the bioelectrical brain signal. In some examples, processor 540 may compare one or more characteristics (e.g., amplitude or frequency) of the bioelectrical brain signal to a threshold associated with activation of the network to determine whether the network is activated.

Memory 541 may store information related to threshold values for signal characteristics that demarcate activation of a particular network for each of the salience and default mode networks and processor 540 may compare characteristics of the sensed bioelectrical brain signals to the stored threshold values to detect network activation.

In various embodiments, system 510 may include one or more external electrodes positioned on the outer surface of the cranium of patient 512 that can sense a bioelectrical brain signal, e.g., an electroencephalogram signal, that can be used to identify activation of a network. Such detection of network activation may use the techniques discussed herein for network activation detection via internally sensed signals (e.g., using a biomarker, template, and/or activation threshold).

Although sensing module 544 is incorporated into a common housing 532 with stimulation generator 542 and processor 540, in other examples, sensing module 544 is in a physically separate outer housing from outer housing 532 of IMD 516 and communicates with processor 540 via wired or wireless communication techniques.

Sensing of brain signals and detecting events such as activation of a brain area or network can be implemented in view of commonly assigned U.S. Provisional Patent Application No. 61/527,387, filed on Aug. 25, 2011, by Carlson et al., titled METHOD AND APPARATUS FOR DETECTING A BIOMARKER IN THE PRESENCE OF ELECTRICAL STIMULATION, which is incorporated by reference herein in its entirety. Furthermore, setting algorithms for event detection, such as training an algorithm to detect activation of a brain area or network, can be implemented in view of commonly assigned U.S. Pat. App. No. 2010/0280335 to Carlson et al., which is entitled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is entitled "PATIENT STATE DETECTION BASED ON SUPPORT VECTOR MACHINE BASED ALGORITHM" filed Nov. 4, 2010, which are incorporated herein by reference in their entireties.

Telemetry module 548 supports wireless communication between IMD 516 and an external programmer 522 or another computing device under the control of processor 540. Processor 540 of IMD 516 may receive, as updates to sensing and/or stimulation programs, values for stimulation parameters such as amplitude and electrode combination information from programmer 522 via telemetry module 548. The updates to the stimulation, sensing, or other programs may be stored within stimulation programs 552 of memory 541. Telemetry module 548 in IMD 516, as well as telemetry modules in other devices and systems described herein, such as programmer 522, may accomplish communication by RF communication techniques. In addition, telemetry module 548 may communicate with external medical device programmer 522 via proximal inductive interaction of IMD 516 with programmer 522. Accordingly, telemetry module 548 may send information to external programmer 522 on a continuous basis, at periodic intervals, or upon request from IMD 516 or programmer 522. For example, processor 540 may transmit sensed signals and/or network activation information to programmer 522 via telemetry module 548.

Power source 550 delivers operating power to various components of IMD 516. Power source 550 may include a small rechargeable or non-rechargeable battery and a power generation circuit to produce the operating power. Recharging may be accomplished through proximal inductive interaction between an external charger and an inductive charging coil within IMD 516. In various embodiments, non-rechargeable primary cell batteries may be used.

Figure 6:
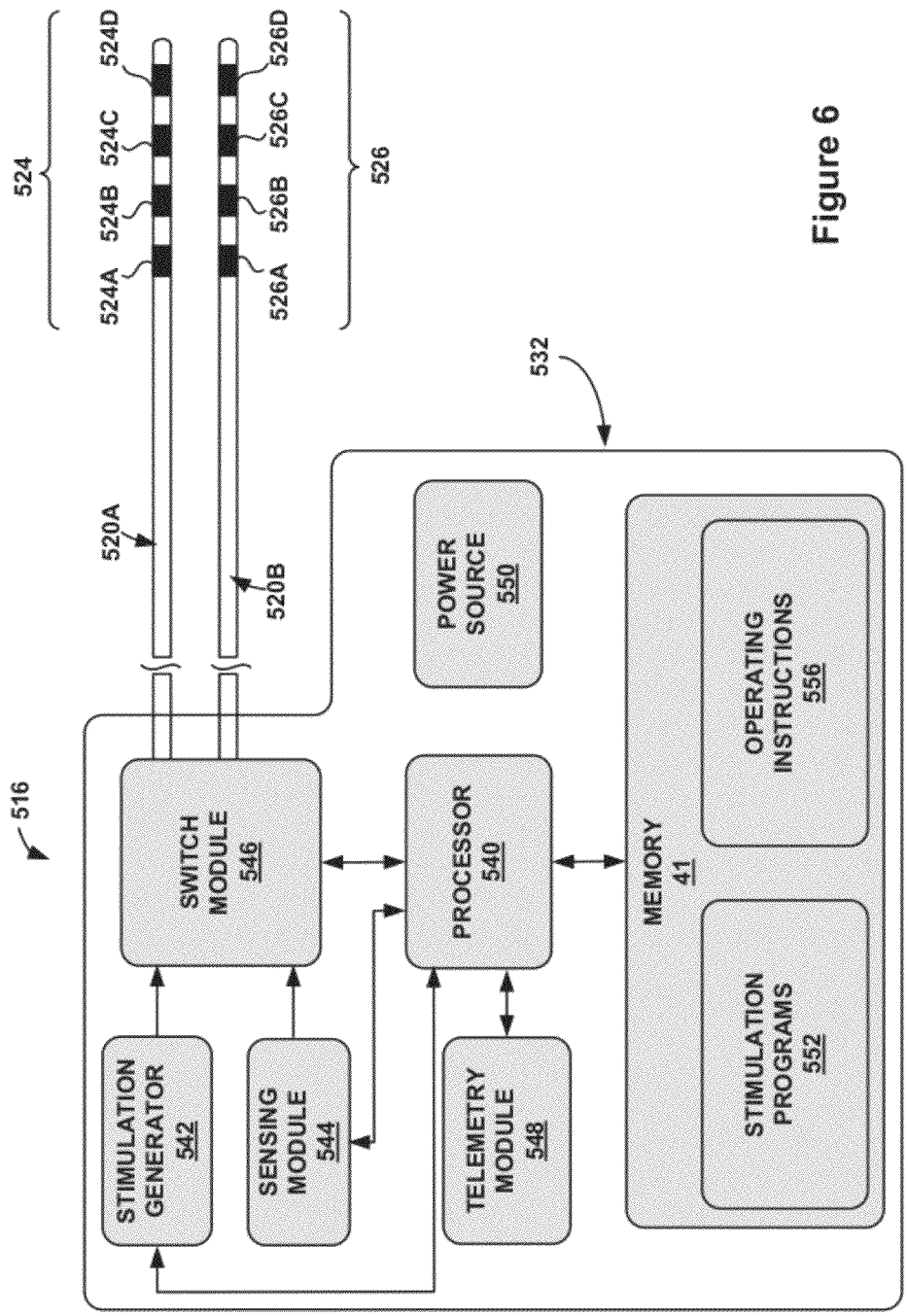
FIG. 6 is a functional block diagram illustrating components of an implantable medical device.

Although the control circuitry of FIG. 6 is generally illustrated and described in terms of an implantable medical device, the control circuitry could alternatively be embodied in an at least partially external device and, depending on the therapy and/or circuitry configuration, may be wholly external. Control circuitry may therefore be embodied in a programmer, desktop computer, and/or server implementation. In various embodiments, control circuitry is part of an imaging system, such as an fMRI medical device. Control circuitry may be distributed between two or more devices, such as an implantable medical device and an external programmer.

The techniques described in this disclosure, including those of FIGS. 1-6 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor for identifying one or more episodes of co-activation and delivering a therapy based on the identification in any referenced herein). The functions referenced herein and those functions of FIGS. 1-6, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

While Alzheimer's disease is generally used as an exemplar for describing various aspects of the present disclosure, it is contemplated that the techniques and devices could be applied to other brain conditions, such as Parkinson's disease, mild cognitive impairment, and traumatic brain damage, among others. Furthermore, it is contemplated that various brain conditions may be characterized by the inappropriate co-activation of two (or more) different brain networks (not necessarily the default mode and salience networks), such as brain networks that ordinarily function in an antagonistic fashion. For example, embodiments of the present disclosure can include monitoring one or more first areas of the patient's brain, each of the one or more first areas associated with providing a first network function for the patient's brain, identifying one or more episodes of first network activation of the one or more first areas, the identified one or more episodes of first network activation associated with the first network function, monitoring one or more second areas of the patient's brain, each of the one or more second areas associated with providing a second function for the patient's brain, wherein the one or more first areas of the patient's brain are different than the one or more second areas of the patient's brain, identifying one or more episodes of second network activation of the one or more second areas, the identified one or more episodes of second network activation associated with the second network function, identifying a plurality of episodes of temporal co-activation of the first and second brain areas based on the identification of the one or more episodes of first network activation and the identification of the one or more episodes of second network activation, and tracking a condition of the patient's brain based on the plurality of episodes of temporal co-activation. Such embodiments can include controlling a therapy based on the identification of an episode of co-activation and/or tracking of the brain condition based on multiple episodes of co-activation. One having ordinarily skill in the art will appreciate that the various techniques, options, features, and components discussed herein are applicable to such embodiments, such as in implementation by an IMD or other device having appropriately configured circuitry. Various applications of monitoring and tracking of co-activation of two brain areas can include monitoring and tracking of co-activation of two (or more) brain areas each associated with default mode network function. Such embodiments can track whether two brain areas are co-activating to support default mode network function. Such co-activation may be indicative of a healthy and coordinated brain in some cases. In some other cases, co-activation of two different brain areas associated with default mode network function may be indicative of a brain disorder (e.g., inappropriate co-activation of two brain areas each associated with default mode network function). In the case of a disorder, electrical stimulation or another therapy can be delivered to prevent activation of one or both areas (e.g., stimulation to suppress a first area when the second area intrinsically activates) or to promote activation of one or both areas (e.g., stimulation to activate a first area when the second area intrinsically activates). Whether indicative of a healthy brain or a disorder, tracking the synchronicity and/or strength (e.g., signal amplitude) of the co-activation can further be used to track a brain condition and/or control a therapy.

It will be appreciated that the various techniques, features, and components discussed herein in various embodiments are applicable to various other embodiments in different configurations and combinations, as the present disclosure makes use of examples to illustrate options which are not limited to the specific embodiments presented. As such, each example embodiment should be understood to be selectively combinable and modifiable in view of the other embodiments presented herein.

I claim:

1. A method for tracking a condition of a patient's brain, the method comprising:
    monitoring one or more first areas of the patient's brain, each of the one or more first areas associated with providing default mode network function for the patient's brain;
    identifying, by control circuitry, one or more episodes of default mode network activation of the one or more first areas, the identified one or more episodes of default mode network activation associated with default mode network function;
    monitoring one or more second areas of the patient's brain, each of the one or more second areas associated with providing salience network function for the patient's brain, wherein the one or more first areas of the patient's brain are different from the one or more second areas of the patient's brain;
    identifying, by the control circuitry, one or more episodes of salience network activation of the one or more second areas, the identified one or more episodes of salience network activation associated with salience network function;
    identifying a plurality of episodes of temporal co-activation of the first and second brain areas based on the identification of the one or more episodes of default mode network activation and the identification of the one or more episodes of salience network activation;
    tracking a condition of the patient's brain based on the plurality of episodes of temporal co-activation, wherein identifying the plurality of episodes of temporal co-activation and tracking the condition are each performed at least in part by the control circuitry; and
    controlling, using the control circuitry, a therapy based on the identification of the plurality of episodes of temporal co-activation of the first and second brain areas.

2. The method of claim 1, wherein:
    identifying the one or more episodes of default mode network activation comprises identifying the one or more episodes of default mode network activation based on a first signal crossing a first threshold indicative of default mode network activation; and
    identifying the one or more episodes of salience network activation comprises identifying the one or more episodes of salience network activation based on a second signal crossing a second threshold indicative of salience network activation.

3. The method of claim 2, further comprising dynamically changing the first threshold based on the second signal and dynamically changing the second threshold based on the first signal.

4. The method of claim 1, wherein monitoring the one or more first areas of the patient's brain and monitoring the one or more second areas of the patient's brain comprises sensing one or more bioelectrical brain signals.

5. The method of claim 1, wherein monitoring the one or more first areas of the patient's brain and monitoring the one or more second areas of the patient's brain comprises imaging the patient's brain with one or more of functional magnetic resonance imagining (fMRI), magnetoencephalogram (MEG), and positron emission tomography (PET).

6. The method of claim 1, wherein identifying each of the episodes of temporal co-activation of the first and second brain areas comprises identifying each of the episodes of temporal co-activation based on temporal co-activation occurring for at least a predetermined period of time.

7. The method of claim 1, wherein tracking the condition of the patient's brain based on the plurality of episodes of temporal co-activation comprises identifying the presence of a disease.

8. The method of claim 1, wherein tracking the condition comprises measuring progression of a disease state based on one or both of frequency and duration of the plurality of episodes of temporal co-activation.

9. The method of claim 1, wherein the condition comprises Alzheimer's disease.

10. The method of claim 1, wherein controlling the therapy comprises controlling administration of the therapy based on the tracking of the condition of the patient's brain.

11. The method of claim 1, wherein controlling a therapy comprises titrating the therapy that treats the condition based on whether the tracking of the condition of the patient's brain indicates a worsening or easing of the condition.

12. The method of claim 1, further comprising:
determining at least one parameter of co-activation, the at least one parameter of co-activation comprising one of:
a time parameter quantifying the amount of time per day the default network and salience network are temporally co-activated, or
a frequency parameter quantifying a number of episodes of temporal co-activation occurring in a predetermined time period, and
storing the at least one parameter of co-activation in a memory.

13. The method of claim 1, further comprising generating electrical stimulation therapy, and wherein controlling the therapy comprises controlling delivery of electrical stimulation therapy.

14. A system comprising:
one or more sensors configured to receive one or more signals indicative of brain activity; and
control circuitry configured to:
detect one or more episodes of default mode network activation based on the one or more signals,
detect one or more episodes of salience network activation based on the one or more signals,
identify one or more episodes of temporal co-activation of the default mode network and the salience network based on the detected one or more episodes of default mode network activation and the detected one or more episodes of salience network activation, and
control a therapy based on the identification of the one or more episodes of temporal co-activation of the default mode network and the salience network.

15. The system of claim 14, wherein the control circuitry is configured to:
track a brain condition based on the identification of the one or more episodes of temporal co-activation of the default mode network and the salience network; and
indicate a worsening of the brain condition based on an increase in one or both of frequency and duration of the one or more episodes of temporal co-activation.

16. The system of claim 14, wherein the control circuitry is configured to:
detect each of the one or more episodes of default mode network activation based on a first parameter of the one or more of signals crossing a first threshold indicative of default mode network activation; and
detect each of the one or more episodes of salience network activation based on a second parameter of the one or more of signals crossing a second threshold indicative of salience network activation.

17. The system of claim 14, wherein the one or more signals comprise bioelectrical brain signals.

18. The system of claim 14, wherein:
the one or more sensors are part of a brain imaging system;
the control circuitry configured to detect the one or more episodes of default mode network activation based on activation of one or more brain areas associated with default mode network function; and
the control circuitry configured to detect the one or more episodes of salience network activation based on activation of one or more brain areas associated with salience network function.

19. The system of claim 14, wherein the control circuitry is configured to identify each of the one or more episodes of temporal co-activation based on temporal co-activation of the default mode network and the salience network that persists for at least a predetermined period of time.

20. The system claim 14, wherein the control circuitry is further configured to:
determine at least one parameter of co-activation, the at least one parameter of co-activation comprising one of:
a time parameter quantifying the amount of time per day the default network and salience network are temporally co-activated, or
a frequency parameter quantifying a number of episodes of temporal co-activation occurring in a predetermined time period, and
store the at least one parameter of co-activation in a memory.

21. The system claim 14, further comprising a stimulation generator configured to generate electrical stimulation therapy, and wherein the control circuitry is configured to control the therapy by at least controlling delivery of electrical stimulation therapy by the stimulation generator.

22. The system of claim 21, wherein the control circuitry is further configured to control the delivery of electrical stimulation therapy to suppress the default mode network.

23. The system of claim 21, wherein the control circuitry is further configured to control the delivery of electrical stimulation therapy to suppress the salience network.

24. The system of claim 21, wherein the control circuitry is further configured to control the delivery of electrical stimulation therapy at a frequency of between 80-140 Hz.

25. The system of claim 14, wherein the control circuitry is configured to control a drug pump to deliver drug therapy.

26. A system, comprising:
means for sensing one or more signals indicative of brain activity;
means for detecting one or more episodes of default mode network activation based on the one or more signals;
means for detecting one or more episodes of salience network activation based on the one or more signals;
means for identifying one or more episodes of temporal co-activation of the default mode network and the salience network based on the detected one or more episodes of default mode network activation and the one or more episodes of salience network activation; and
means for controlling a therapy based on identification, by the means for identifying, of the one or more episodes of temporal co-activation of the default mode network and the salience network.

27. The system of claim 26, further comprising means for tracking a brain condition based on the identification of the one or more episodes of temporal co-activation of the default mode network and the salience network, wherein a worsening brain condition is indicated based on an increase in one or both of frequency and duration of the one or more episodes of temporal co-activation.

28. The system of claim 26, further comprising:
- means for determining at least one parameter of co-activation, the at least one parameter of co-activation comprising one of:
  - a time parameter quantifying the amount of time per day the default network and salience network are temporally co-activated, or
  - a frequency parameter quantifying a number of episodes of temporal co-activation occurring in a predetermined time period, and
- means for storing the at least one parameter of co-activation.

29. The system of claim 26, further comprising means for generating electrical stimulation therapy, and wherein the means for controlling the therapy controls the means for generating the electrical stimulation therapy based on the identification of the one or more episodes of temporal co-activation of the default mode network and the salience network.

* * * * *